United States Patent
Kim et al.

(10) Patent No.: US 9,566,323 B2
(45) Date of Patent: Feb. 14, 2017

(54) VACCINE FOR CERVICAL CANCER

(75) Inventors: Hong-Jin Kim, Seoul (KR); Na Gyong Lee, Seoul (KR); Yang-Je Cho, Seoul (KR); Jin-Wook Jang, Seoul (KR); Hyoung Jin Kim, Seoul (KR); Kwang Sung Kim, Hanam-si (KR)

(73) Assignee: Eyegene Inc., Seoul (KR)

( * ) Notice: Subject to any disclaimer, the term of this patent is extended or adjusted under 35 U.S.C. 154(b) by 0 days.

(21) Appl. No.: 13/379,212

(22) PCT Filed: Oct. 20, 2009

(86) PCT No.: PCT/KR2009/006062
§ 371 (c)(1),
(2), (4) Date: Dec. 19, 2011

(87) PCT Pub. No.: WO2010/147268
PCT Pub. Date: Dec. 23, 2010

(65) Prior Publication Data
US 2012/0100169 A1   Apr. 26, 2012

(30) Foreign Application Priority Data
Jun. 19, 2009 (KR) .................. 10-2009-0055179

(51) Int. Cl.
A61K 39/12 (2006.01)
A61K 39/39 (2006.01)
A61K 39/00 (2006.01)

(52) U.S. Cl.
CPC ............ *A61K 39/12* (2013.01); *A61K 39/39* (2013.01); *A61K 2039/5258* (2013.01); *A61K 2039/55505* (2013.01); *A61K 2039/55572* (2013.01); *A61K 2039/70* (2013.01); *C12N 2710/20023* (2013.01); *C12N 2710/20034* (2013.01)

(58) Field of Classification Search
None
See application file for complete search history.

(56) References Cited

U.S. PATENT DOCUMENTS

| 6,685,949 | B1* | 2/2004 | Gu et al. ............ 424/251.1 |
| 7,507,802 | B2* | 3/2009 | Ahn et al. ............ 536/23.1 |
| 2005/0042230 | A1* | 2/2005 | Anderson et al. ...... 424/186.1 |
| 2006/0251676 | A1 | 11/2006 | Dubin et al. |

FOREIGN PATENT DOCUMENTS

| EP | 1 410 805 A1 | 4/2004 |
| WO | WO 2004/039413 A1 | 5/2004 |
| WO | WO 2006/121232 A1 | 11/2006 |

OTHER PUBLICATIONS

Villa LL et al. Immunologic responses following administration of a vaccine targeting human papillomavirus Types 6, 11, 16, and 18. Vaccine. Jul. 7, 2006;24(27-28):5571-83. Epub May 15, 2006.*
Giannini SL et al. Enhanced humoral and memory B cellular immunity using HPV16/18 L1 VLP vaccine formulated with the MPL/aluminium salt combination (AS04) compared to aluminium salt only. Vaccine. Aug. 14, 2006;24(33-34):5937-49. Epub Jun. 19, 2006.*
Liu X et al. Gonococcal lipooligosaccharide suppresses HIV infection in human primary macrophages through induction of innate immunity. J Infect Dis. Sep. 15, 2006;194(6):751-9. Epub Aug. 8, 2006.*
Molecular Probes, Product Information, p. 1-3, revised Jan. 6, 2003.*
Chen et al. Papillomavirus virus like particle-based therapeutic vaccine against human papillomavirus infection related diseases: immunological problems and future directions. Cell Immunol. 2011;269(1):5-9. Epub Mar. 12, 2011.*
Schenck et al. The Enhancement of antibody Formation by *E. coli* lipopolysaccharide and Detoxified derivatives. J Immunol 1969; 102:1411-1422.*

* cited by examiner

*Primary Examiner* — Nick Zou
(74) *Attorney, Agent, or Firm* — Clark & Elbing LLP; Susan M. Michaud

(57) ABSTRACT

The present invention relates to a pharmaceutical vaccine composition for a human cervical cancer, comprising: (a) (i) a L1 virus-like particle (VLP) of human papillomavirus (HPV) type 16, a L1 VLP of HPV type 18, or a combination thereof; and (ii) a deacylated non-toxic lipooligosaccharide (LOS); and (b) a pharmaceutically acceptable carrier; and a method for preparing a human papillomavirus (HPV) L1 virus-like particle (VLP). The pharmaceutical vaccine composition of the present invention is in both Th1-type immune response (cellular immunity) and Th2-type immune response (humoral immunity) against HPV more excellent than Cervrix™ and Gardasil™, exhibiting a superior efficacy as a vaccine for a human cervical cancer.

5 Claims, 30 Drawing Sheets

SEQUENCE LISTING

<160> NUMBER OF SEQ ID NOS: 4

<210> SEQ ID NO 1
<211> LENGTH: 1518
<212> TYPE: DNA
<213> ORGANISM: Artificial Sequence
<220> FEATURE:
<223> OTHER INFORMATION: YEG-HPV16-ROS
<220> FEATURE:
<221> NAME/KEY: CDS
<222> LOCATION: (1)..(1515)

<400> SEQUENCE: 1

```
atg tcg tta tgg tta cct tca gaa gct acc gtt tat ctt cct cca gta     48
Met Ser Leu Trp Leu Pro Ser Glu Ala Thr Val Tyr Leu Pro Pro Val
1               5                   10                  15 cca gtt tcc aaa gtc gtt tct aca gat gaa tac gtt gct aga act aac     96
Pro Val Ser Lys Val Val Ser Thr Asp Glu Tyr Val Ala Arg Thr Asn
                20                  25                  30 att tac tac cat gca ggc act tcc agg tta tta gct gtc ggt cat ccc    144
Ile Tyr Tyr His Ala Gly Thr Ser Arg Leu Leu Ala Val Gly His Pro
            35                  40                  45 tat ttc cca att aaa aag ccc aac aat aat aag ata tta gtt cca aaa    192
Tyr Phe Pro Ile Lys Lys Pro Asn Asn Asn Lys Ile Leu Val Pro Lys
        50                  55                  60 gtt tcc ggc tta caa tac aga gtc ttt aga ata cat tta cca gat cct    240
Val Ser Gly Leu Gln Tyr Arg Val Phe Arg Ile His Leu Pro Asp Pro
65                  70                  75                  80 aac aag ttc ggt ttt cca gat aca agt ttt tat aac cct gat aca caa    288
Asn Lys Phe Gly Phe Pro Asp Thr Ser Phe Tyr Asn Pro Asp Thr Gln
                85                  90                  95 cgt tta gtt tgg gca tgt gtt ggt gtt gaa gtg ggc cgt ggt caa cct    336
Arg Leu Val Trp Ala Cys Val Gly Val Glu Val Gly Arg Gly Gln Pro
                100                 105                 110 ctt ggc gtc ggg att tct ggt cac cca tta ttg aat aag tta gac gat    384
Leu Gly Val Gly Ile Ser Gly His Pro Leu Leu Asn Lys Leu Asp Asp
            115                 120                 125 act gaa aac gcc tcc gcc tac gct gct aac gca gga gtc gac aat agg    432
Thr Glu Asn Ala Ser Ala Tyr Ala Ala Asn Ala Gly Val Asp Asn Arg
        130                 135                 140 gaa tgc att tca atg gac tat aaa caa act caa cta tgc tta att ggt    480
Glu Cys Ile Ser Met Asp Tyr Lys Gln Thr Gln Leu Cys Leu Ile Gly
145                 150                 155                 160 tgt aaa cct cca att ggt gaa cat tgg ggt aaa gga tct ccc tgc acg    528
Cys Lys Pro Pro Ile Gly Glu His Trp Gly Lys Gly Ser Pro Cys Thr
                165                 170                 175 aat gtt gca gtt aat cct ggt gat tgt cca ccc tta gaa ttg att aat    576
Asn Val Ala Val Asn Pro Gly Asp Cys Pro Pro Leu Glu Leu Ile Asn
                180                 185                 190 act gtt ata caa gat ggt gac atg gtc gat acc ggc ttc gga gct atg    624
Thr Val Ile Gln Asp Gly Asp Met Val Asp Thr Gly Phe Gly Ala Met
            195                 200                 205 gac ttt act aca tta caa gcg aat aaa tca gaa gtt ccg cta gat att    672
Asp Phe Thr Thr Leu Gln Ala Asn Lys Ser Glu Val Pro Leu Asp Ile
        210                 215                 220
```

```
tgt act tcc att tgt aaa tac cca gat tac att aag atg gtg tct gaa      720
Cys Thr Ser Ile Cys Lys Tyr Pro Asp Tyr Ile Lys Met Val Ser Glu
225                 230                 235                 240 cct tat ggt gat tca cta ttt ttc tac ctg cgt cgt gaa caa atg ttt      768
Pro Tyr Gly Asp Ser Leu Phe Phe Tyr Leu Arg Arg Glu Gln Met Phe
                245                 250                 255 gtt aga cat ctt ttc aat cgt gct gga gcc gta gga gaa aat gta cca      816
Val Arg His Leu Phe Asn Arg Ala Gly Ala Val Gly Glu Asn Val Pro
            260                 265                 270 gat gat tta tat ata aaa ggt tcc ggt tct aca gca aat tta gcc tca      864
Asp Asp Leu Tyr Ile Lys Gly Ser Gly Ser Thr Ala Asn Leu Ala Ser
        275                 280                 285 tca aat tat ttc cca acc cca tca ggt tca atg gtt act tca gac gcg      912
Ser Asn Tyr Phe Pro Thr Pro Ser Gly Ser Met Val Thr Ser Asp Ala
    290                 295                 300 caa att ttt aat aaa ccc tat tgg ctt caa agg gct caa ggt cat aac      960
Gln Ile Phe Asn Lys Pro Tyr Trp Leu Gln Arg Ala Gln Gly His Asn
305                 310                 315                 320 aat ggt att tgt tgg ggc aat cag tta ttc gtc aca gtc gtc gat act     1008
Asn Gly Ile Cys Trp Gly Asn Gln Leu Phe Val Thr Val Val Asp Thr
                325                 330                 335 act aga tca act aat atg agt tta tgt gca gca ata tcc act tca gaa     1056
Thr Arg Ser Thr Asn Met Ser Leu Cys Ala Ala Ile Ser Thr Ser Glu
            340                 345                 350 acc act tat aag aat acc aac ttt aaa gaa tac ttg aga cac ggt gaa     1104
Thr Thr Tyr Lys Asn Thr Asn Phe Lys Glu Tyr Leu Arg His Gly Glu
        355                 360                 365 gaa tat gac ttg caa ttc atc ttt caa tta tgc aaa atc act tta aca     1152
Glu Tyr Asp Leu Gln Phe Ile Phe Gln Leu Cys Lys Ile Thr Leu Thr
    370                 375                 380 gca gac gta atg aca tat att cat tca atg aac tct aca att tta gaa     1200
Ala Asp Val Met Thr Tyr Ile His Ser Met Asn Ser Thr Ile Leu Glu
385                 390                 395                 400 gat tgg aac ttc gga cta caa cct cct cca ggc gga aca cta gaa gac     1248
Asp Trp Asn Phe Gly Leu Gln Pro Pro Pro Gly Gly Thr Leu Glu Asp
                405                 410                 415 act tat aga ttt gtt acc tca cag gcc atc gca tgt caa aag cat aca     1296
Thr Tyr Arg Phe Val Thr Ser Gln Ala Ile Ala Cys Gln Lys His Thr
            420                 425                 430 cca cca gcg ccg aaa gaa gac ccc ttg aaa aaa tac act ttc tgg gaa     1344
Pro Pro Ala Pro Lys Glu Asp Pro Leu Lys Lys Tyr Thr Phe Trp Glu
        435                 440                 445 gtt aac ttg aaa gaa aaa ttc tct gct gat tta gat caa ttt cca tta     1392
Val Asn Leu Lys Glu Lys Phe Ser Ala Asp Leu Asp Gln Phe Pro Leu
    450                 455                 460 gga cgt aaa ttt tta cta caa gca ggt tta aaa gct aag cca aaa ttc     1440
Gly Arg Lys Phe Leu Leu Gln Ala Gly Leu Lys Ala Lys Pro Lys Phe
465                 470                 475                 480 acc cta ggc aaa aga aaa gca aca cct act act tct tcc aca tct aca     1488
Thr Leu Gly Lys Arg Lys Ala Thr Pro Thr Thr Ser Ser Thr Ser Thr
                485                 490                 495 act gcc aaa aga aaa aag aga aaa ttg taa                             1518
Thr Ala Lys Arg Lys Lys Arg Lys Leu
            500                 505

<210> SEQ ID NO 2
<211> LENGTH: 505
<212> TYPE: PRT
<213> ORGANISM: Artificial Sequence
<220> FEATURE:
<223> OTHER INFORMATION: Synthetic Construct
```

```
<400> SEQUENCE: 2

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
                100                 105                 110

Leu Gly Val Gly Ile Ser Gly His Pro Leu Leu Asn Lys Leu Asp Asp
            115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
```

```
                       405                 410                 415
Thr Tyr Arg Phe Val Thr Ser Gln Ala Ile Ala Cys Gln Lys His Thr
                420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
        450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
                500                 505

<210> SEQ ID NO 3
<211> LENGTH: 1524
<212> TYPE: DNA
<213> ORGANISM: Artificial Sequence
<220> FEATURE:
<223> OTHER INFORMATION: YEG-HPV18L1-ROS
<220> FEATURE:
<221> NAME/KEY: CDS
<222> LOCATION: (1)..(1521)

<400> SEQUENCE: 3 atg gcc ctt tgg aga cct tca gac aat act gtg tac ctt ccc cct cct      48
Met Ala Leu Trp Arg Pro Ser Asp Asn Thr Val Tyr Leu Pro Pro Pro
1               5                   10                  15 tct gtc gct aga gta gta aac aca gat gat tac gta act aga aca tct      96
Ser Val Ala Arg Val Val Asn Thr Asp Asp Tyr Val Thr Arg Thr Ser
            20                  25                  30 att ttt tac cac gcc ggt agc tca aga tta tta aca gta ggt aat cct     144
Ile Phe Tyr His Ala Gly Ser Ser Arg Leu Leu Thr Val Gly Asn Pro
        35                  40                  45 tat ttc cgt gtc cca gca ggc ggc ggt aat aaa caa gac att cct aaa     192
Tyr Phe Arg Val Pro Ala Gly Gly Gly Asn Lys Gln Asp Ile Pro Lys
    50                  55                  60 gtc tca gcc tac caa tat aga gta ttc aga gtc caa ctt ccc gat ccc     240
Val Ser Ala Tyr Gln Tyr Arg Val Phe Arg Val Gln Leu Pro Asp Pro
65                  70                  75                  80 aac aaa ttt gga ttg cca gac acg tcg ata tat aac cca gaa aca cag     288
Asn Lys Phe Gly Leu Pro Asp Thr Ser Ile Tyr Asn Pro Glu Thr Gln
                85                  90                  95 aga cta gtt tgg gcc tgt gca gga gtt gaa ata gga aga gga caa ccc     336
Arg Leu Val Trp Ala Cys Ala Gly Val Glu Ile Gly Arg Gly Gln Pro
            100                 105                 110 ttg ggc gta ggt tta tca ggt cac ccc ttc tac aat aaa tta gac gat     384
Leu Gly Val Gly Leu Ser Gly His Pro Phe Tyr Asn Lys Leu Asp Asp
        115                 120                 125 aca gaa tct agc cat gca gcc aca agt aat gtt tca gag gat gta agg     432
Thr Glu Ser Ser His Ala Ala Thr Ser Asn Val Ser Glu Asp Val Arg
    130                 135                 140 gac aat gtt tcc gta gac tat aaa cag acc caa cta tgt ata tta ggt     480
Asp Asn Val Ser Val Asp Tyr Lys Gln Thr Gln Leu Cys Ile Leu Gly
145                 150                 155                 160 tgt gct cca gca att ggc gaa cac tgg gct aag gga act gcg tgc aaa     528
Cys Ala Pro Ala Ile Gly Glu His Trp Ala Lys Gly Thr Ala Cys Lys
                165                 170                 175 tca agg ccc cta tca caa ggc gat tgt ccc ccc tta gaa tta aaa aac     576
Ser Arg Pro Leu Ser Gln Gly Asp Cys Pro Pro Leu Glu Leu Lys Asn
```

```
                    180                 185                 190
aca gtc tta gaa gat gga gat atg gtc gat acc ggt tat ggc gca atg        624
Thr Val Leu Glu Asp Gly Asp Met Val Asp Thr Gly Tyr Gly Ala Met
        195                 200                 205 gat ttt tca aca tta caa gac acg aag tgt gaa gtg ccc cta gat att        672
Asp Phe Ser Thr Leu Gln Asp Thr Lys Cys Glu Val Pro Leu Asp Ile
210                 215                 220 tgt caa tca att tgt aaa tac cct gac tac tta caa atg tct gcc gac        720
Cys Gln Ser Ile Cys Lys Tyr Pro Asp Tyr Leu Gln Met Ser Ala Asp
225                 230                 235                 240 cca tat ggc gac tcc atg ttt ttt tgc ttg aga aga gaa caa tta ttt        768
Pro Tyr Gly Asp Ser Met Phe Phe Cys Leu Arg Arg Glu Gln Leu Phe
                245                 250                 255 gct cgt cat ttt tgg aac cgt gca gga aca atg ggt gat aca gtt cct        816
Ala Arg His Phe Trp Asn Arg Ala Gly Thr Met Gly Asp Thr Val Pro
            260                 265                 270 caa tct tta tat ata aaa ggc aca ggc atg cgt gct tcc cct ggt tcg        864
Gln Ser Leu Tyr Ile Lys Gly Thr Gly Met Arg Ala Ser Pro Gly Ser
        275                 280                 285 tgc gta tat tct cct tca ccg tca ggt tct att gtc acg tca gat agt        912
Cys Val Tyr Ser Pro Ser Pro Ser Gly Ser Ile Val Thr Ser Asp Ser
    290                 295                 300 caa tta ttt aac aaa cca tat tgg tta cat aaa gct caa ggt cat aat        960
Gln Leu Phe Asn Lys Pro Tyr Trp Leu His Lys Ala Gln Gly His Asn
305                 310                 315                 320 aat ggt gta tgt tgg cac aat caa tta ttc gta act gta gtc gat aca       1008
Asn Gly Val Cys Trp His Asn Gln Leu Phe Val Thr Val Val Asp Thr
                325                 330                 335 acc aga tcc act aat tta aca ata tgt gca tca act cag tca ccc gtt       1056
Thr Arg Ser Thr Asn Leu Thr Ile Cys Ala Ser Thr Gln Ser Pro Val
            340                 345                 350 cca ggt caa tat gac gca aca aaa ttc aaa caa tac tcc aga cat gta       1104
Pro Gly Gln Tyr Asp Ala Thr Lys Phe Lys Gln Tyr Ser Arg His Val
        355                 360                 365 gaa gaa tac gac tta caa ttc att ttc cag cta tgt act atc acg tta       1152
Glu Glu Tyr Asp Leu Gln Phe Ile Phe Gln Leu Cys Thr Ile Thr Leu
    370                 375                 380 aca gcc gat gtc atg tct tat att cac tct atg aac tcc tct att tta       1200
Thr Ala Asp Val Met Ser Tyr Ile His Ser Met Asn Ser Ser Ile Leu
385                 390                 395                 400 gaa gat tgg aac ttt ggc gtt cca cca cct ccc act aca tca tta gtc       1248
Glu Asp Trp Asn Phe Gly Val Pro Pro Pro Pro Thr Thr Ser Leu Val
                405                 410                 415 gat aca tac cgt ttc gtt caa tct gtt gcc atc act tgt caa aaa gac       1296
Asp Thr Tyr Arg Phe Val Gln Ser Val Ala Ile Thr Cys Gln Lys Asp
            420                 425                 430 gca gcc ccc gca gaa aat aaa gac cca tac gat aaa tta aaa ttt tgg       1344
Ala Ala Pro Ala Glu Asn Lys Asp Pro Tyr Asp Lys Leu Lys Phe Trp
        435                 440                 445 aat gta gat ctt aag gaa aaa ttt agt tta gac tta gat cag tat cct       1392
Asn Val Asp Leu Lys Glu Lys Phe Ser Leu Asp Leu Asp Gln Tyr Pro
    450                 455                 460 tta gga aga aaa ttt ctt gtt caa gca ggt ctg aga aga aaa cca acc       1440
Leu Gly Arg Lys Phe Leu Val Gln Ala Gly Leu Arg Arg Lys Pro Thr
465                 470                 475                 480 atc ggc cca aga aaa aga tcc gca cct tct gcc act aca tca tca aaa       1488
Ile Gly Pro Arg Lys Arg Ser Ala Pro Ser Ala Thr Thr Ser Ser Lys
                485                 490                 495 cca gcc aaa aga gta aga gta aga gct aga aag taa                       1524
Pro Ala Lys Arg Val Arg Val Arg Ala Arg Lys
```

```
Pro Ala Lys Arg Val Arg Val Arg Ala Arg Lys
            500                 505
```

<210> SEQ ID NO 4
<211> LENGTH: 507
<212> TYPE: PRT
<213> ORGANISM: Artificial Sequence
<220> FEATURE:
<223> OTHER INFORMATION: Synthetic Construct

<400> SEQUENCE: 4

```
Met Ala Leu Trp Arg Pro Ser Asp Asn Thr Val Tyr Leu Pro Pro Pro
1               5                   10                  15

Ser Val Ala Arg Val Val Asn Thr Asp Asp Tyr Val Thr Arg Thr Ser
            20                  25                  30

Ile Phe Tyr His Ala Gly Ser Ser Arg Leu Leu Thr Val Gly Asn Pro
        35                  40                  45

Tyr Phe Arg Val Pro Ala Gly Gly Asn Lys Gln Asp Ile Pro Lys
    50                  55                  60

Val Ser Ala Tyr Gln Tyr Arg Val Phe Arg Val Gln Leu Pro Asp Pro
65                  70                  75                  80

Asn Lys Phe Gly Leu Pro Asp Thr Ser Ile Tyr Asn Pro Glu Thr Gln
                85                  90                  95

Arg Leu Val Trp Ala Cys Ala Gly Val Glu Ile Gly Arg Gly Gln Pro
            100                 105                 110

Leu Gly Val Gly Leu Ser Gly His Pro Phe Tyr Asn Lys Leu Asp Asp
        115                 120                 125

Thr Glu Ser Ser His Ala Ala Thr Ser Asn Val Ser Glu Asp Val Arg
    130                 135                 140

Asp Asn Val Ser Val Asp Tyr Lys Gln Thr Gln Leu Cys Ile Leu Gly
145                 150                 155                 160

Cys Ala Pro Ala Ile Gly Glu His Trp Ala Lys Gly Thr Ala Cys Lys
                165                 170                 175

Ser Arg Pro Leu Ser Gln Gly Asp Cys Pro Pro Leu Glu Leu Lys Asn
            180                 185                 190

Thr Val Leu Glu Asp Gly Asp Met Val Asp Thr Gly Tyr Gly Ala Met
        195                 200                 205

Asp Phe Ser Thr Leu Gln Asp Thr Lys Cys Glu Val Pro Leu Asp Ile
    210                 215                 220

Cys Gln Ser Ile Cys Lys Tyr Pro Asp Tyr Leu Gln Met Ser Ala Asp
225                 230                 235                 240

Pro Tyr Gly Asp Ser Met Phe Phe Cys Leu Arg Arg Glu Gln Leu Phe
                245                 250                 255

Ala Arg His Phe Trp Asn Arg Ala Gly Thr Met Gly Asp Thr Val Pro
            260                 265                 270

Gln Ser Leu Tyr Ile Lys Gly Thr Gly Met Arg Ala Ser Pro Gly Ser
        275                 280                 285

Cys Val Tyr Ser Pro Ser Pro Ser Gly Ser Ile Val Thr Ser Asp Ser
    290                 295                 300

Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Val Asp Thr
                325                 330                 335

Thr Arg Ser Thr Asn Leu Thr Ile Cys Ala Ser Thr Gln Ser Pro Val
            340                 345                 350
```

-continued

```
Pro Gly Gln Tyr Asp Ala Thr Lys Phe Lys Gln Tyr Ser Arg His Val
        355                 360                 365
Glu Glu Tyr Asp Leu Gln Phe Ile Phe Gln Leu Cys Thr Ile Thr Leu
    370                 375                 380
Thr Ala Asp Val Met Ser Tyr Ile His Ser Met Asn Ser Ser Ile Leu
385                 390                 395                 400
Glu Asp Trp Asn Phe Gly Val Pro Pro Pro Thr Thr Ser Leu Val
                405                 410                 415
Asp Thr Tyr Arg Phe Val Gln Ser Val Ala Ile Thr Cys Gln Lys Asp
            420                 425                 430
Ala Ala Pro Ala Glu Asn Lys Asp Pro Tyr Asp Lys Leu Lys Phe Trp
        435                 440                 445
Asn Val Asp Leu Lys Glu Lys Phe Ser Leu Asp Leu Asp Gln Tyr Pro
    450                 455                 460
Leu Gly Arg Lys Phe Leu Val Gln Ala Gly Leu Arg Arg Lys Pro Thr
465                 470                 475                 480
Ile Gly Pro Arg Lys Arg Ser Ala Pro Ser Ala Thr Thr Ser Ser Lys
                485                 490                 495
Pro Ala Lys Arg Val Arg Val Arg Ala Arg Lys
            500                 505
```

VACCINE FOR CERVICAL CANCER

CROSS-REFERENCE TO RELATED APPLICATIONS

This application is the U.S. national stage filing under 35 U.S.C. §371 of international application PCT/KR2009/006062, filed Oct. 20, 2009, which claims benefit of Korean Patent Application 10-2009-0055179, filed Jun. 19, 2009.

BACKGROUND OF THE INVENTION

Field of the Invention

The present invention relates to a pharmaceutical vaccine composition for a human cervical cancer, a method for preventing a human cervical cancer, and a method for preparing a human papillomavirus (HPV) L1 virus-like particle (VLP).

Description of the Related Art

More than 80 types of Human Papillomavirus (HPV) have been known and about 30 types causes cervical infection through sexual contact, of which half types have been known to be related with cervical cancer (Zur Hausen H, Mol. Carcinogenesis 8: 147-150 (1988)). Of them, it has been known that a cancer rate of women infected with HPV type 16 and 18 is about 50-fold higher than that of normal women, and HPV type 16 and 18 are infected into epithelial cells of genital organ, resulting in cervical cancer via malignant transformation (Zur Hausen H, Mol. Carcinogenesis 8: 147-150 (1988); Hausen, Biochemica. Biophysica. Acta. 1288: 55-78 (1996)).

Current vaccines for preventing a cervical cancer have been developed using high risk type HPV virus-like particles (VLPs). VLP is a major capsid protein (L1 protein, about 55 kDa) of HPV, and has various advantages as a vaccine candidate, including: (a) an ability self-assembled to VLP without gene product of other virus like that as observed in natural HPV virion; (b) maintenance of long-term immunity; and (c) a highly efficiency due to a type specificity against a gene type.

'Gardasil' (Merck & Co., Inc.) using VLPs is a vaccine developed using each antigen against HPV type 6, 11, 16 and 18, and 'Alum' as the most common immunoadjuvant. 'Cervarix' (GlaxoSmithKline Plc.) is a vaccine developed using HPV type 16 and 18 as a representative factor triggering a cervical cancer and 'AS04' as an immunoadjuvant developed independently.

Alum used as an immunoadjuvant in the 'gardasil' has been utilized as a vaccine for diphtheria, tetanus and hepatitis type B, and it was reported that Alum enhances antigen stability and induces release of cytokines. However, the use of gardasil is limited because: (a) it is impossible to lyophilize or freeze vaccine; (b) it is not effective in all antigens; and (c) it promotes only humoral immune response.

AS04 contained in the Cervarix of GSK has been developed for the purpose of inducing potent and persistent immune responses, and is composed of aluminum hydroxide and monophosphoryl lipid A (MPL). The term "MPL" used herein refers to an immunostimulatory substance capable of directly activating a critical immune response, playing a role in enhancement of immune response against an antigen involved in the vaccine.

Recently, immunoadjuvants have been newly focused and utilized in various vaccines such as cervical cancer vaccines and influenza vaccines. Of them, bacterial DNA received attention as an anti-cancer agent since 1960's, and is successively researched up to now. However, bacterial DNA has not been used as an anti-cancer agent due to its low efficacy (Glick, J. L. The specificity of inhibition of tumor cell viability by DNA. Cancer Res. 27: 2338 (1967)). In spite of this defect, it was demonstrated that bacterial DNA is known to activate various immune cells without serious side effects, and has many advantages as an adjuvant (McCluskie M J, et al., CpG DNA is a potent enhancer of systemic and mucosal immune responses against hepatitis B surface antigen with intranasal administration to mice. J Immunol. November 1; 161 (9): 4463-6 (1998)).

For these effects of bacterial DNA, Yamamoto et al. in Japan argument that palindromic sequences containing CG play a crucial role in effects of bacterial DNA which are demonstrated by Krieg et al. (Yamamoto S. et al. Unique palindromic sequences in synthetic oligonucleotides are required to induce IFN and augment IFN-mediated natural killer activity. 3. Immunol. 148: 4072 (1992); Krieg A M, Antitumor applications of stimulating toll-like receptor 9 with CpG oligodeoxynucleotides. Curr. Oncol. Rep. March; 6 (2): 88-95 (2004)). Based on CpG-related studies from the middle of 1990's, the concern for DNA anti-cancer agent leaded to deduce a probability of synthetic DNA (CpG-ODN) containing unmethylated CG as an anti-cancer agent, for example a study for S substitution in diester bonds to inhibit short synthetic DNA degradation. In this connection, CpG-ODN-related products were utilized in a clinical trial as an anti-cancer agent as well as an adjuvant (colevpharma).

However, there remains to be solved some problems including immunogenicity and still low anti-cancer activity of S substitution in diester bonds of CpG-ODN. On current clinic, CpG 7909 is a phosphothioate oligonucleotide which induces anti-DNA Ab (Clin Immunol. August; 100 (2): 157-63 (2001)), and is closely associated with autoimmune disorders such as SLE (systemic lupus erythematosus) (J Clin Immunol. July; 6 (4): 292-8 (1986)). In addition, it has been known that phosphothioate structure functions as TI Ag, contributing to disturbance of immune protection against infections (Mol Immunol. December; 35 (18): 1161-70 (1998)).

In LPS known to have anti-cancer effect since 1950's, utilization of LPS was difficult because LPS in a range of ng results in death by sepsis. It is general opinion that the link between LPS and DNA causes serious cytotoxicity, and thus the elimination of LPS is understood as very important process in DNA-related medicaments (Gao J J. et. al, Bacterial DNA and lipopolysaccharide induce synergistic production of TNF-alpha through a post-transcriptional mechanism. J Immunol 166 (11): 6855-60 (2001)). In respect with efficacies, it should be considered that immune responses stimulated by LPS are much stronger than those by DNA whereas are Th2-type responses, not Th1-type which is important to anti-cancer, supposing LPS is not suitable as an anti-cancer agent (Lebman DA et at Interleukin 4 causes isotype switching to IgE in T cell-stimulated clonal B cell cultures. 3 Exp Med. September 1; 168 (3): 853-62 (1988)). Given that Th2-type immune activity inhibits Th1-type immune activity, it was very difficult to utilize LPS as an anti-cancer agent due to Th2-type immune activity stimulated by LPS (Rengarajan J et al. Transcriptional regulation of Th1/Th2 polarization. Immunol Today. October; 21 (10): 479-83 (2000)).

A variety of attempts to LPS detoxification have been studied, leading to successfully reduce its cytotoxicity through removal of polysaccharide chain or deacylation of lipid A (Katz S S et al Deacylation of lipopolysaccharide in whole *Escherichia coli* during destruction by cellular and extracellular components of a rabbit peritoneal inflammatory exudate. J Biol Chem. December 17; 274 (51): 36579-84 (1999)). For example, monophosphoryl lipid A (MPL) is obtained by phosphorylation of lipid A in which polysaccharide chain of LPS is eliminated to develop an immunotherapeutic anti-cancer agent. However, its efficacy is known to be quite low (corixa).

On the other hand, the present applicants have already developed a novel immunoadjuvant to complement drawbacks of the above-mentioned immunoadjuvants (Korean Patent No. 0740237 (2007.07.10)).

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

The present inventors have done intensive studies to develop a novel vaccine which may overcome problems of conventional vaccines for a cervical cancer as described above. As results, we have discovered that a non-toxic LOS (lipooligosaccharide), which a portion of fatty acid is removed from lipid A, may be used as an immunoadjuvant in immunization using L1 VLP of HPV type 16 or 18, whereby HPV immune responses are induced much more notable than those by conventional VLP-based vaccines, enabling to function as an excellent vaccine for preventing a human cervical cancer.

Accordingly, it is an object of this invention to provide a pharmaceutical vaccine composition for a human cervical cancer It is another object of this invention to provide a method for preventing a human cervical cancer.

It is still another object to this invention to provide a method for preparing a HPV L1 VLP.

It is further still another object to this invention to provide a novel nucleic acid sequence encoding a L1 VLP of a HPV type 16.

It is further still another object to this invention to provide a novel nucleic acid sequence encoding a L1 VLP of a HPV type 18.

It is another object of this invention to provide a *Saccharomyces cerevisiae* transformed with the novel nucleic acid sequence as described above.

Other objects and advantages of the present invention will become apparent from the following detailed description together with the appended claims and drawings.

In one aspect of this invention, there is provided a pharmaceutical vaccine composition for a human cervical cancer, comprising: (a) (i) a L1 virus-like particle (VLP) of human papillomavirus (HPV) type 16, a L1 VLP of HPV type 18, or a combination thereof; and (ii) a deacylated non-toxic lipooligosaccharide (LOS); and, (b) a pharmaceutically acceptable carrier.

In another aspect of this invention, there is provided a method for preventing a human cervical cancer, comprising administering to a human the pharmaceutical composition as described above.

The present inventors have done intensive studies to develop a novel vaccine which may overcome problems of conventional vaccines for a cervical cancer as described above. As results, we have discovered that a non-toxic LOS (lipooligosaccharide), which a portion of fatty acid is removed from lipid A, may be used as an immunoadjuvant in immunization using L1 VLP of HPV type 16 or 18, whereby HPV immune responses are induced much more notable than those by conventional VLP-based vaccines, enabling to function as an excellent vaccine for preventing a human cervical cancer.

VLP used in the pharmaceutical composition of the present invention is derived from L1 VLP of HPV type 16 or 18. HPV type 16 or 18 is known to be high risk types of HPV, and is a representative HPV which induces a cervical cancer.

The term "HVP L1 protein" used herein refers to a major protein in HPV capsid, which is expressed from a L1 gene of HPV. L1 protein may be self-assembled in itself or with L2 protein, another minor protein constituting HPV capsid, under suitable condition.

VLP used in the present invention includes total sequences encoding a natural occurring L1 protein of HPV type 16 or 18, and a functional L1 protein derivative thereof. As used herein, the term "functional HPV L1 derivative" means a natural occurring HPV L1 protein derivative which is capable of forming VLP and inducing immune responses although its sequence is not equal to total sequences encoding a natural occurring HPV L1 protein. For example, the functional HPV L1 derivative is a truncated L1 protein in which a nuclear localization signal is removed. Another example of HPV L1 protein capable of being used in the present invention includes a L1 protein of HPV type 16 which 34 amino acids of C-terminal are removed, or a L1 protein of HPV type 18 which 35 amino acids of C-terminal are eliminated. Illustrative example of amino acid sequence encoding L1 VLP of HPV type 16 or 18 is described in SEQ ID NO:2 and SEQ ID NO:4, respectively.

As an antigen inducing immune response in the pharmaceutical composition of this invention, HPV16 L1 VLP or HPV18 L1 VLP is used, preferably both.

Alternatively, in addition to HPV16 L1 VLP or HPV18 L1 VLP, L1 VLP as an antigen may further include at least one L1 VLP selected from the group consisting of L1 VLPs of HPV type 31, HPV type 45, HPV type 6a, HPV type 6b, HPV type 11, HPV type 33, HPV type 35, HPV type 39, HPV type 51, HPV type 52, HPV type 56, HPV type 58 and HPV type 68.

Alternatively, L1 VLP used in the present invention may be fused with other protein, for example L2 protein.

It is the most feature of the present pharmaceutical composition to utilize a deacylated non-toxic LOS (lipooligosaccharide) as an immunoadjuvant. The term "LOS (lipooligosaccharide)" adapted first herein refers to a modifier of LPS (lipopolysaccharide) with low molecular weight which has glycochains shorter than natural occurring LPS. LOS has a molecular weight in a range of 5,000-10,000 Da before deacylation. The term "deacylated LOS" used herein means a form of LOS that a fatty acid linked to glucosamine of lipid A via —C(O)O— bond is eliminated from LOS, resulting in significant reduction of cytotoxicity compared to LOS. The fatty acid is linked to glucosamine of lipid A through —C(O)O— bond and —C(O)NH— bond. The deacylated LOS of the present invention is a LOS of which the fatty acid linked by —C(O)O— bond is removed by deacylation of lipid A.

The deacylated non-toxic LOS of the present invention may be prepared according to various methods, for example methods disclosed in previous patents of the present inventors including Korean Patent No. 0456681; WO 2004/039413; Korean Patent No. 0740237; and WO 2006/121232. For instance, a portion of fatty acid in LOS is removed and detoxificated from lipid A through deacylation via strong base treatment (e.g., 2 N NaOH) to LPS (lipopolysaccharide).

According to a preferable embodiment, the deacylated non-toxic LOS used as an immunoadjuvant in the present invention is detoxificated by deacylation of lipid A via alkaline treatment to LPS (lipopolysaccharide). Preferred example of the alkaline treatment includes NaOH, KOH, $Ba(OH)_2$, CsOH, $Sr(OH)_2$, $Ca(OH)_2$, LiOH, RbOH and $Mg(OH)_2$, more preferably NaOH, KOH, $Ba(OH)_2$, $Ca(OH)_2$, LiOH and $Mg(OH)_2$, much more preferably NaOH, KOH and $Mg(OH)_2$, and most preferably NaOH.

The detoxification extent of LPS may be analyzed according to various methods known to those ordinarily skilled in the art. For example, the detoxification may be determined by measuring an amount of TNF-$\alpha$ (tumor necrosis factor-$\alpha$) secreted in THP-1 (acute monocytic leukemia) treated with LPS. The deacylated non-toxic LOS of the present invention induces a relatively little amount of TNF-$\alpha$ secretion compared with conventional LPS.

It is another feature that the deacylated non-toxic LOS of the present invention has lower molecular weight than conventional LPS to be used in general. Preferably, the deacylated non-toxic LOS used in the present invention has a molecular weight in a range of 1,500-10,000 Da, more preferably 2,000-5,000 Da, much more preferably 2,000-4,000 Da, still much more preferably 3,000-4,000 Da, and most preferably 3,200-3,700 Da. Measurement of molecular weight may be carried out using a conventional method, for example MALDI-MASS.

According to a preferable embodiment, the deacylated non-toxic LOS of this invention is derived from *Escherichia coli* (*E. coli*), and most preferably *E. coli* EG0021 (KCCM 10374) isolated by the present inventors.

The deacylated non-toxic LOS used in the present invention is very suitable for the vaccine composition of this invention due to much excellent immunostimulatory effect and significantly low cytotoxicity compared with conventional immunoadjuvants. As demonstrated in Examples below, the deacylated non-toxic LOS of this invention has much lower cytotoxicity than monophosphoryl lipid A (MPL) obtained through phosphorylation of lipid A from which a polysaccharide chain of LPS is removed to reduce LPS cytotoxicity.

As shown in Example below (See, FIGS. 12a-12b), the administration of the deacylated non-toxic LOS of the present invention with HPV L1 VLP also induces the level of IgG1 related to Th2-type immune response (humoral immunity) as well as IgG2a related to Th1-type immune response (cellular immunity), demonstrating that the deacylated non-toxic LOS of the present invention may synergistically induce immune responses together with HPV L1 VLP.

The vaccine composition of the present invention may contribute to a preventive efficacy on a cervical cancer only in a fundamental composition containing HPV 16 L1 VLP, HPV 18 L1 VLP or a combination thereof, and deacylated non-toxic LOS. Alternatively, the vaccine composition of the present invention may further include other immunoadjuvant, for example including a Group II element selected from the group consisting of Mg, Ca, Sr, Ba and Ra; a Group IV element selected from the group consisting of Ti, Zr, Hf and Rf; or an aluminium salt or a hydrate thereof. Preferably, the salt is formed with oxide, peroxide, hydroxide, carbonate, phosphate, pyrophosphate, hydrogen phosphate, dihydrogen phosphate, sulfate or silicate. For example, the immunoadjuvant capable of being additionally used in the vaccine composition of the present invention includes magnesium hydroxide, magnesium carbonate hydroxide, pentahydroxide, titanium dioxide, calcium carbonate, barium oxide, barium hydroxide, barium peroxide, barium sulfate, calcium sulfate, calcium pyrophosphate, magnesium carbonate, magnesium oxide, aluminum hydroxide, aluminum phosphate and hydrated aluminum potassium sulfate (Alum). Most preferably, the immunoadjuvant capable of being additionally used in the vaccine composition of the present invention is aluminum hydroxide.

According to a preferable embodiment, the L1 VLP of HPV type 16 or 18 is obtained by a purification procedure including the steps of: (i) culturing yeasts containing a HPV L1-encoding nucleotide sequence of HPV type 16 or 18; (ii) lysing the cultured yeast; (iii) precipitating the yeast lysate with ammonium sulfate to eliminate impurities; and (iv) performing a heparin chromatography or cation-exchange chromatography in the yeast lysate which the impurities are removed.

The detailed descriptions of the purification procedure are described below.

In the pharmaceutical vaccine compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered via the oral or parenterally. When the pharmaceutical composition of the present invention is administered parenterally, it can be done by intravenous, subcutaneous, intramuscular, abdominal and transdermal administration.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Preferably, the pharmaceutical composition of the present invention is administered with a daily dose of 0.0001-1,000 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

The pharmaceutical vaccine composition of the present invention induces strong immune responses against HPV than conventional vaccines including Cervrix™ and Gardasil™, and thus has excellent potency for preventing a cervical cancer. In addition, the pharmaceutical vaccine composition of the present invention possesses superior stability because the deacylated non-toxic LOS used as an immunoadjuvant in the present invention has almost no cytotoxicity.

As demonstrated in Examples below, not only the level of interferon-γ, IgG2a and IgG2b related to Th1-type immune response (cellular immunity) but also the level of IgG1 related to Th2-type immune response (humoral immunity) is strikingly enhanced in the administration of the pharmaceutical vaccine composition of the present invention than in the administration of Cervrix™ and Gardasil™. In other words, the pharmaceutical vaccine composition of the present invention may induce both Th1-type immune response (cellular immunity) and Th2-type immune response (humoral immunity) against HPV more excellent than Cervrix™ and Gardasil™.

In still another aspect of this invention, there is provided a method for preparing a human papillomavirus (HPV) L1 virus-like particle (VLP), comprising the steps of:

(i) culturing yeasts containing a HPV L1-encoding nucleotide sequence;

(ii) lysing the cultured yeast;

(iii) precipitating the yeast lysate with ammonium sulfate to eliminate impurities; and, (iv) performing a heparin chromatography or cation-exchange chromatography in the yeast lysate which the impurities are removed.

The present inventors have done intensive studies to develop a purification method that a procedure to produce HPV VLPs is simplified and a yield rate of HPV VLPs is enhanced in yeast expression system of HPV VLPs for preparing a vaccine against HPV. As results, we have discovered that excellent purification efficiency (yield rate and purity) may be obtained where a yeast lysate is precipitated with ammonium sulfate and then a heparin chromatography or cation-exchange chromatography is carried out.

Below, this invention is described in detail according to the step:

(i) Culture of transformed yeast expressing a HPV L1 protein

According to the method of the present invention, the L1 protein-derived HPV type is not particularly restricted, and includes HPV type 6a, HPV type 6b, HPV type 11, HPV type 16, HPV type 18, HPV type 31, HPV type 33, HPV type 35, HPV type 39, HPV type 45, HPV type 51, HPV type 52, HPV type 56, HPV type 58 and HPV type 68, but is not limited to. Preferably, the L1 protein of the present invention is derived from HPV selected from the group consisting of HPV type 6a, HPV type 6b, HPV type 11, HPV type 16, HPV type 18, HPV type 31, HPV type 33 and HPV type 45, and more preferably, HPV type 16 and HPV type 18.

Cells used as a host cell in the present invention is yeast, for example including, but not limited to, baker's yeast, *Saccharomyces cerevisiae*, *Saccharomyces pastorianus*, *Saccharomyces* sp., *Schizosaccharomyces pombe*, and so forth. Most preferably, the host yeast of this invention is *Saccharomyces cerevisiae*.

Transformed yeast expressing HPV L1 protein refers to a yeast cell transformed with an expression vector which successfully expresses a HPV L1 protein. Various promoters known to those skilled in the art, for example including GAL1 promoter, GAL10 promoter (Johnson, M., and Davies, R. W., Mol. and Cell. Biol., 4: 1440-1448 (1984)), ADH2 promoter (Russell, D., et al., J. Biol. Chem., 258: 2674-2682, (1983)), PH05 promoter (EMBO J. 6: 675-680, (1982)) or MFal promoter may be linked to the upstream of HPV L1 gene to be expressed in the expression vector, and a polyadenylation sequence including ADHI, MFaI or TPI-derived poly A sequence (Alber, T. and Kawasaki, G., J. Mol. & Appl. Genet. 1: 419-434 (1982)) may be involved in the expression vector. As a yeast expression vector, YEp6, YEpl3, YEp4 and YEGα (S. N. Kim, et al., J. Virol. Methods 139 (2007) 24-30; R. Kirnbauer, et al., J Virol 67 (1993) 6929-6936) are well-known in the art. Transformed yeast to express HPV L1 protein may be prepared according to various methods known to those skilled in the art, for example including U.S. Pat. Nos. 7,250,170, 6,613,557, 5,888,516, 5,871,998, 5,618,536 and 5,437,951, which are incorporated herein by reference.

According to a preferable embodiment, the transformed yeast is cultured in a medium supplemented with one or more carbon sources of glucose and galactose. According to another preferable embodiment, the ratio of glucose and galactose is a weight ratio of glucose:galactose=0-1:3-4, more preferably glucose:galactose=0.5-1:3.5-4, and most preferably, glucose:galactose=1:3. The expression of HPV L1 protein may be maximized where the weight ratio of glucose and galactose used in the media of the present invention is in a range as described above.

Exemplified medium used in the culture of transformed yeast is a YPDG medium including yeast extract, peptone, glucose and galactose.

(ii) Lysis of the Cultured Yeast

The lysis method of the cultured yeast in the present invention is not restricted to a particular method, preferably a lysis method to obtain whole lysate of yeast cells. For example, the lysis method capable of being used in the present invention includes, but is not limited to, a sonication or a homogenization using glass beads.

(iii) Ammonium Sulfate Precipitation to Eliminate Impurities of the Yeast Lysate The expressed proteins were precipitated and the impurities were removed by adding ammonium sulfate to the yeast lysate.

According to a preferable embodiment, the concentration of ammonium sulfate to be added is in a range of 20-60 wt %, more preferably 40-50 wt %, and most preferably, 42-48 wt %. Where the concentration of ammonium sulfate is in a range of not more than 40 wt %, the precipitation efficiency of HPV L1 protein expressed in this invention is lowered. The precipitation efficiency of HPV L1 protein expressed in this invention is not enhanced depending on increase of ammonium sulfate where the concentration of ammonium sulfate is in a range of not less than 50 wt %.

Alternatively, the protein pellet obtained by ammonium sulfate precipitation is lysed, and mixed with NaCl of not less than 0.5 M, followed by incubating at 4° C. for at least 12 hrs.

(iii-2) Elimination of Impurities in Low-Concentrated Salt (e.g., NaCl)

The solution obtained from the step (iii) is dialyzed in a buffer containing low-concentrated salt (e.g., NaCl), and then incubated at room temperature for removing impurities in an insoluble state.

According to a practical example of the present invention, the concentration of the low-concentrated salt is used in a range of 0.001-0.3 M, more preferably 0.01-0.2 M, and most preferably, 0.1-0.8 M, and the salt to be used is selected from the group consisting of NaCl, KCl, $MgCl_2$, $CaCl_2$, $Na_2SO_4$ and $(NH_4)_2SO_4$, and most preferably, NaCl.

According to a preferable embodiment, the process to treat the low-concentrated salt is carried out in the presence of a non-ionic sulfactant. For example, the non-ionic sulfactant includes polyoxyalkylene sorbitan fatty acid ester, sorbitan fatty acid ester, alkylene glycol fatty acid ester, polyoxyalkylene fatty acid ester, fatty acid ester, polyoxyalkylene fatty acid ether, $C_{16-24}$ fatty acid, fatty acid mono-, di- or poly-glyceride, polyoxyalkylene alkyl phenol, alkyl phenyl ether, polyoxyethylene-polyoxypropylene block copolymer, fatty acid amine oxide, fatty acid alkanolamide, alkyl cellulose, carboxyalkyl cellulose or polyoxyalkylene castor oil derivates, and preferably, polyoxyethylene sorbitan mono- or tri-lauryl, palmityl, stearyl or oleyl ester such as polyoxyethylene (20) sorbitan monolaurate (Tween-20), polyoxyethylene (4) sorbitan monolaurate (Tween-21), polyoxyethylene (20) sorbitan monopalmitate (Tween-40), polyoxyethylene (20) sorbitan monostearate (Tween-60), polyoxyethylene (20) sorbitan tristearate (Tween-65) or polyoxyethylene (20) sorbitan monooleate (Tween-85). In addition, it is preferable to treat a non-ionic sulfactant with a concentration of 0.001-0.01%.

The step to treat low-concentrated NaCl as described above is very efficient to eliminate impurities, and significantly contributes to shortening of procedure and improvement of purification efficiency in the method of the present invention.

The insoluble proteins produced in the step are removed by centrifugation, resulting in noticeably increasing purity of VLP to be eluted through a heparin chromatography or cation-exchange chromatography. Therefore, it is shown that the step plays an excellent role in enhancement of purification efficiency by eliminating impurities in a simple manner.

(iv) Heparin Chromatography or Cation-Exchange Chromatography

Heparin chromatography or cation-exchange chromatography is carried out in the solution which impurities are removed.

In purification of the solution which impurities are removed using a heparin chromatography or cation-exchange chromatography as described above, the impurities may be eliminated in a very efficient manner.

In the step carrying out a heparin chromatography, the solution of step (iii) or (iii-2) is equilibrated with a binding buffer suitable for heparin resin before loading into a heparin resin column. Preferably, the binding buffer includes NaCl and non-ionic sulfactant (e.g., Tween-80), and NaCl is used in low concentration (0.1-0.2 M). Afterwards, the sample is applied to a heparin chromatography, and then the proteins are eluted from the resin. Elution method is preferable to use linear NaCl gradient. More preferably, impurities are eluted in linear gradient of NaCl (0.33-0.66 M), and then desirable L1 protein is eluted in linear gradient of NaCl (0.66-2 M).

The cation-exchange chromatography may be performed using various resins, preferably a cation-exchanger linked with sulfo, sulfoalkyl (e.g., sulfomethyl, sulfoethyle and sulfopropyl), phosphate or phosphate alkyl functional group, and most preferably phosphate functional group. In the step carrying out a cation-exchange chromatography, the solution of step (iii) or (iii-2) is equilibrated with a binding buffer suitable for heparin resin before loading into a heparin resin column. Preferably, the binding buffer includes NaCl and non-ionic sulfactant (e.g., Tween-80), and NaCl is used in low concentration (0.3-0.4 M). Later, the sample is applied to a cation-exchange chromatography, and then the proteins are eluted from the resin. Elution method is preferable to use step NaCl gradient. More preferably, desirable L1 protein is eluted using an elution buffer containing NaCl of 0.6 M, 0.7 M, 0.8 M and 1 M.

(v) Concentration

According to a preferable embodiment, the L1 protein fraction obtained through chromatography as described above is concentrated with a membrane filter. Preferably, the chromatography fraction is concentrated by passing a membrane capable of having a cut-off function of proteins with the molecular weight of 50-100 kDa. Since VLP having a size mean of about 50 nm is a large protein compared with other proteins, it is concentrated without passing the membrane whereas most of residual impurities are removed through passing the membrane. Thus, the step not only increases the purity of HPV 16 L1 protein, but also enhances the concentration of HPV 16 L1 protein The preparation method of the present invention utilized a method removing impurities by treating a cell homogenate under particular conditions before performing the chromatography step of this invention, leading to maximize a purification efficiency of L1 protein. The cell homogenate is precipitated with ammonium sulfate to primarily eliminate impurities, and then incubated under the condition of low-concentrated salt for secondary removal of impurities. The method as described above may permit to remove about 80% of impurities and to retrieve not less than 80% of L1 protein, contributing to enhancement of purity in a simple manner. Therefore, the method of the present invention has diverse advantages such as: (a) purification of L1 protein with high purity without performing various chromatography steps; (b) remarkably saving time, cost and labor necessary for protein production where this method is applied to production and purification in a pilot and industrial scale.

In another aspect of this invention, there is provided a nucleic acid sequence encoding a L1 virus-like particle (VLP) of a human papillomavirus (HPV) type 16 comprising a nucleotide sequence of SEQ ID NO:1. In addition, this invention provides a nucleic acid sequence encoding a L1 virus-like particle (VLP) of a human papillomavirus (HPV) type 18 comprising a nucleotide sequence of SEQ ID NO:3.

In still another aspect of this invention, there is provided a *Saccharomyces cerevisiae* (deposit number: KCCM11036P) transformed with the nucleic acid sequence encoding the L1 virus-like particle (VLP) of the human papillomavirus (HPV) type 16 as described above. In addition, this invention provides a *Saccharomyces cerevisiae* (deposit number: KCCM11037P) transformed with the nucleic acid sequence encoding the L1 virus-like particle (VLP) of the human papillomavirus (HPV) type 18 as described above.

The nucleotide sequence of SEQ ID NO:1 and SEQ ID NO:3 is optimized to express a nucleotide sequence encoding HPV L1 protein in a highly efficient manner.

The features and advantages of the present invention will be summarized as follows:

(a) The pharmaceutical vaccine composition for a human cervical cancer utilizes HPV 16 L1 VLP, HPV 18 L1 VLP, or HPV 16 L1 VLP and HPV 18 L1 VLP as an antigen, and a deacylated non-toxic LOS as an immunoadjuvant.

(b) The deacylated non-toxic LOS has a very excellent immunostimulatory effect in immune response against HPV, and a higher stability due to almost no cytotoxicity.

(c) In addition, the deacylated non-toxic LOS synergistically induces immune response against HPV by enhancing both Th1-type immune response (cellular immunity) and Th2-type immune response (humoral immunity).

(d) The pharmaceutical vaccine composition of the present invention is in both Th1-type immune response (cellular immunity) and Th2-type immune response (humoral immunity) against HPV more excellent than Cervrix™ and Gardasil™, exhibiting a superior efficacy as a vaccine for a human cervical cancer.

(e) The preparation method of HPV L1 VLP of the present invention allows purification of L1 protein with high purity through one chromatography step, and has a remarkable effect in saving of time, cost and labor necessary for protein production where this method is applied to production and purification in a pilot and industrial scale.

BRIEF DESCRIPTION OF THE DRAWINGS

FIG. 4 shows the SDS-PAGE result of samples obtained after heparin chromatography without the step of removing the insoluble contaminants. FIG. 5 is the SDS-PAGE result of heparin chromatography according to method 1 in FIG. 3. FIG. 6 is Western blotting result after heparin chromatography. Lanes 1 and 2 are loading samples and unbound samples. Lane 3, 4, 5, 6, 7, 8, 9, 10, 11, 12, 13, 14, 15 and 16 each represents sample fraction 9, 12, 15, 18, 21, 24, 27, 30, 33, 36, 39, 42, 45 and 48. The arrow indicates the molecular weight of the L1 protein.

FIG. 7 shows the SDS-PAGE result of samples obtained by cation-exchange chromatography according to method 2 in FIG. 3. FIG. 8 is Western blotting result after cation-exchange chromatography. Lane 1, 2, and 3 are loading samples, unbound samples and wash samples, respectively. Lane 4, 5, 6, 7, 8 and 9 each represents sample fraction 1, 2, 3, 4, 5, 6. Sample fractions 1, 2, and 3 were eluted with buffer containing 0.6, 0.7 and 0.8 M NaCl, respectively. Sample fractions 4, 5, and 6 were eluted with buffer containing 1 M NaCl. The arrow indicates the molecular weight of the L1 protein.

FIG. 12 shows the SDS-PAGE result of samples obtained after heparin chromatography without the step of removing the insoluble contaminants. FIG. 13 is the SDS-PAGE result of heparin chromatography according to method 1 in FIG. 3. FIG. 14 is Western blotting result after heparin chromatography. Lanes 1 and 2 are loading samples and unbound samples. Lane 3, 4, 5, 6, 7, 8, 9, 10, 11, 12, 13, 14, 15 and 16 each represents sample fraction 9, 12, 15, 18, 21, 24, 27, 30, 33, 36, 39, 42, 45 and 48. The arrow indicates the molecular weight of the L1 protein.

FIG. 15 shows the SDS-PAGE result of samples obtained by cation-exchange chromatography according to method 2 in FIG. 3. FIG. 16 is Western blotting result after cation-exchange chromatography. Lane 1, 2, and 3 are loading samples, unbound samples and wash samples, respectively. Lane 4, 5, 6, 7, 8 and 9 each represents sample fraction 1, 2, 3, 4, 5, 6. Sample fractions 1, 2, and 3 were eluted with buffer containing 0.6, 0.7 and 0.8 M NaCl, respectively. Sample fractions 4, 5, and 6 were eluted with buffer containing 1 M NaCl. The arrow indicates the molecular weight of the L1 protein.

FIG. 23 and FIG. 24 are a graph showing the anti-HPV 16 L1 HPV antibody titer (FIG. 23) and its fold increase (FIG. 24) depending on the various concentrations of novel CIA05, HPV 16 L1 VLP and aluminum peroxide (Alum) in the combination mixture. Open bar is total IgG, diagonal lined bar is IgG1 and close bar is IgG2a.

FIG. 26 is total IgG titer data for HPV 16 L1 VLP and FIG. 27 is total IgG titer data for HPV 18 L1 VLP.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Protein Expression and Purification of Human Papillomavirus Type 16 and 18 VLP L1

Figure 1:
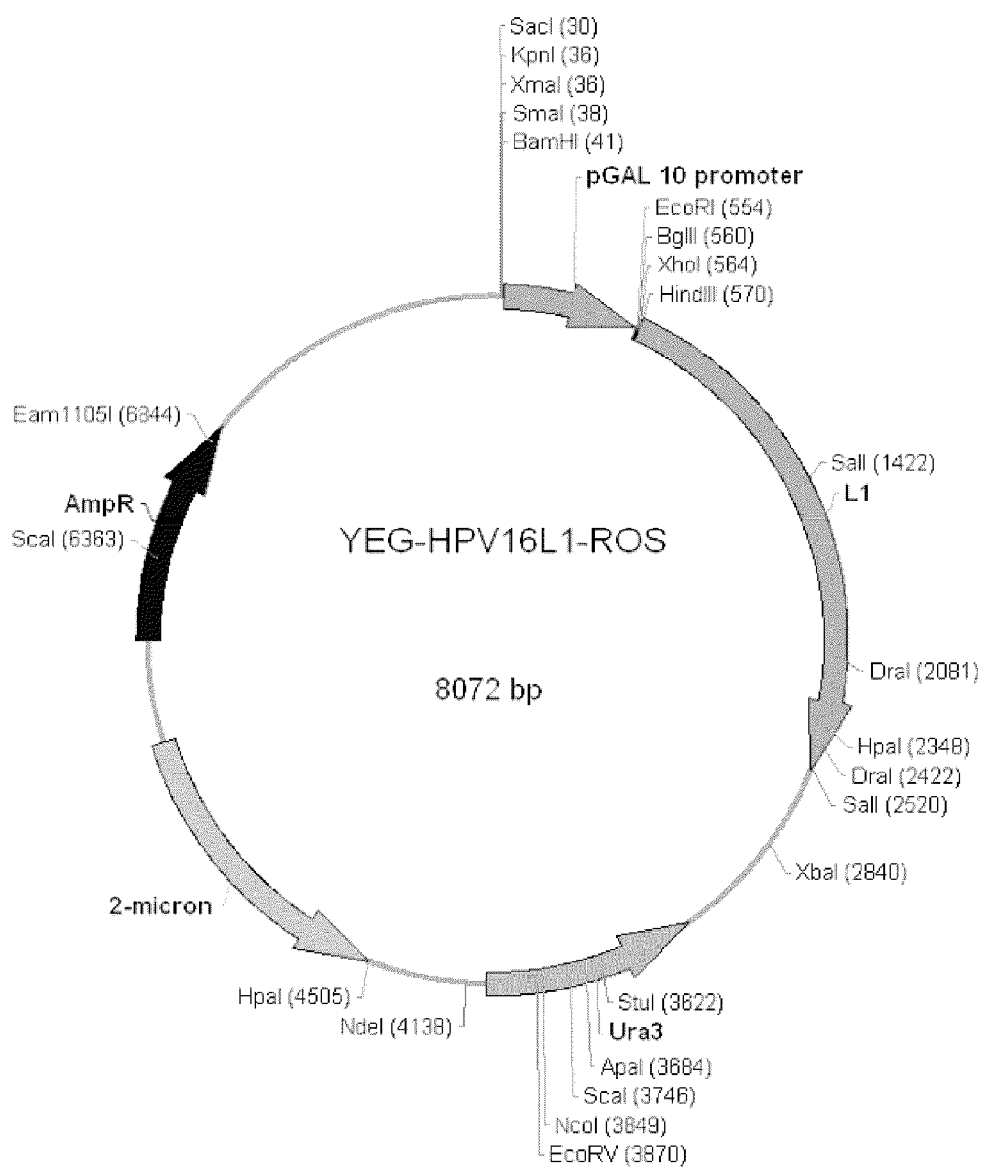
FIG. 1 and FIG. 2 are a DNA map of YEP (yeast expression vector) expressing HPV type 16 and type 18 L1 VLP protein. AmpR is ampicillin resistant gene, Ura3 is a gene for synthesizing orotidine 5-phosphate decarboxylase, 2-micron is the replication origin and the others indicated are the restriction enzyme sites.
Figure 2:
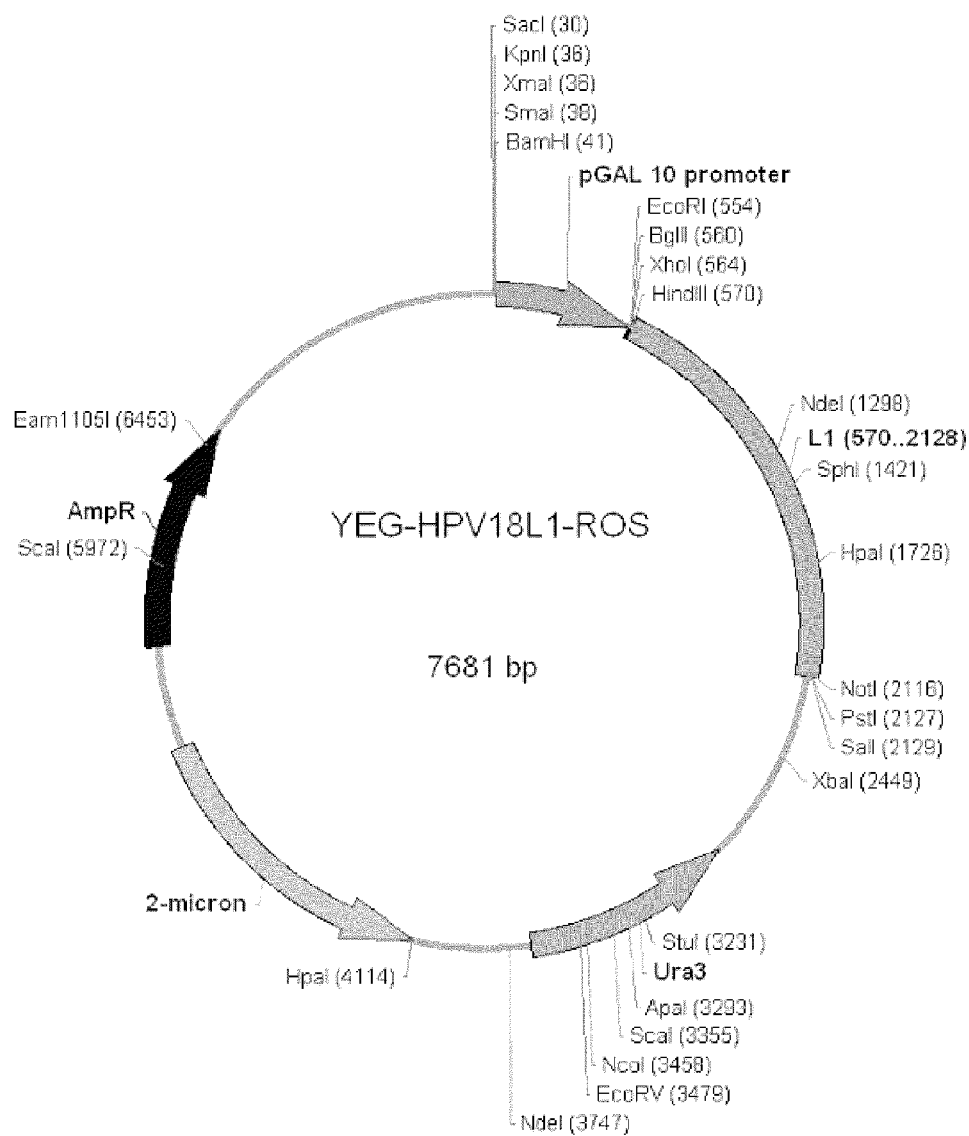

Construction of Recombinant Yeast Expression System Producing HPV Type 16 and 18 L1 protein Using the yeast (Saccharomyces cerevisiae) optimal codon/expression, sequence 1 was selected from the sequence list for HPV type 16 L1 DNA and sequence 3 was selected from the sequence list for HPV type 18 L1 DNA. DNA were synthesized using the "Synthesis in BHB Standard Vectors" service (blueheronbio) (c.f., sequence 1 and sequence 3 from the sequence list). HindIII (AAGCTT) and ClaI (ATCGAT) restriction sites were ligated at both ends of the optimized DNA sequences. The yeast expression vectors, YEG α-HPV16L1 and YEG α-HPV 18L1, for expressing recombinant HPV16L1 and HPV18L1 proteins were constructed by DNA cloning (FIG. 1). Followings are the cloning methods: pUCminusMCS vector (Invitrogen) encoding HPV type 16 L1 DNA (sequence 1, sequence list) or HPV Type 18 L1 DNA (Sequence 3, sequence list) and YEG-MCS yeast expression vector was digested with HindIII and ClaI. The digested DNA was extracted using HiYield™ Gel/PCR DNA Extraction Kit (#YDF100, RBC) after electrophoresis. HPV type 16 or type 18 DNA and YEG-MCS vector was ligated using ligase (TAKARA, 2011a) and introduced into dam(−) E. coli competent cell (TAKARA, 9129). Transformed cells forming colonies were picked, incubated, and their size was confirmed by digesting the purified plasmid with enzymes. Size verified plasmid was transformed into yeast (Saccharomyces cerevisiae) and spread on a SD (−ura) plate. When colonies start to grow, 25 colonies were picked and inoculated in YPDG media (250 rpm, 30° C., shaking for 2 days). The best strain was selected based on its O.D. at incubation, total amount of protein after cell lysis, ELISA and Westernblot analysis after purification (method described below).

Transformed strains with YEG α-HPV16L1-ORS and YEG α-HPV 18L1YEG-ORS vectors encoding recombinant HPV16L1 and HPV18L1 were each submitted for patent depository to Korean Culture Center of Microorganisms on Oct. 8, 2009 with accession numbers KCCM11036P and KCCM11037P (KCCM11036P—Saccharomyces cerevisiae EF0216; KCCM11037P—Saccharomyces cerevisiae EG0218).

Cell Culture

The transformed yeast strains were inoculated and grown in synthetic complete medium lacking uracil (SD-ura; Clontech) by shaking at 30° C. using a baffle attached flask. YPDG medium was used to express HPV16 L1 and HPV18 L1 protein from GAL10 promoter. All media contained 1% yeast extract (DIFCO Laboratories, USA), 2% peptone (DIFCO Laboratories, USA), 1% glucose and 3% galactose. The yeast stain transformed by the plasmid were inoculated in 3L of YPDG medium and incubated for 48 hrs at 30° C.

Preparing Cell Lysate

Cultures were collected by centrifugation and the pellets were stored at −70° C. until use. All the following experiments were performed at 4° C. Cell pellets were resuspended in 100 ml of ice cold breakage buffer (20 mM sodium phosphate, pH 7.2, 100 mM NaCl, 1.7 mM EDTA, 0.01% Tween 80) before adding the protease inhibitor cocktail (Roche, USA). The cells were disrupted with glass beads (Sigma, USA) in a Bead-Beater (Biospec Products, USA) by vortexing for 5 min. The crude extract was then centrifuged at 10,000 g for 10 min at 4° C. to remove unbroken cells.

Ammonium Sulfate Precipitation

HPV L1 protein was obtained from the cleared cell lysate by ammonium sulfate precipitation. The protein pellet was obtained by adding 43% or 45% of ammonium sulfate and stirring for 30 min at 4° C., then centrifuge at 12,000 g for 10 min. The pellet resulting from ammonium sulfate precipitation was resuspended in PBS buffer+0.1% Tween-80, before adding NaCl to a final concentration of 0.5 M or higher. This solution was incubated at 4° C. for at least 12 hrs.

Removing Contaminants by Incubating with Low Concentration of NaCl

The solution incubated with high concentration of NaCl was dialyzed against PBS buffer+0.01% Tween 80 and diluted with sodium phosphate buffer (pH 7.2) containing 0.15 M NaCl and 0.01% Tween 80 to a final protein concentration of 2-5 mg/ml. This solution was left to stand at room temperature for more than 2 hrs for insoluble protein to form. The insoluble protein precipitates were discarded after centrifugation at 10,000 g for 10 min.

Heparin Chromatography

The solution incubated with low concentration of NaCl was centrifuged and the supernatant was dialyzed against binding buffer (PBS buffer+0.2 M NaCl pH 7.0, 0.01% Tween 80). The heparin resin (5 ml or 20 ml) packed column was equilibrated with 5 resin volumes of binding buffer. The dialyzed sample solution was loaded onto the heparin column to bind before washing with 5 resin volumes of the binding buffer. Contaminants were eluted with a linear NaCl gradient starting at 0.33 M and reaching 0.66 M after 35 min. The L1 protein was eluted with a linear NaCl gradient ranging in the concentration from 0.66M to 2 M.

Cation-Exchange Chromatography

The solution incubated with low concentration of NaCl was centrifuged and the supernatant was dialyzed against binding buffer (PBS buffer+0.2 M NaCl pH7.0, 0.01% Tween 80). The 8 cm×4 cm Poly-Prep resin column packed with P-11 cellulose phosphate resin (Whatman, UK) column was equilibrated with 5 resin volumes of the binding buffer. The dialyzed sample solution was loaded onto the P-11 column to bind before washing with 5 resin volumes of the binding buffer. After washing with the binding buffer, L1 protein was stepwise eluted by flowing 4-5 ml of the elution buffer, which was the binding buffer containing 0.6 M, 0.7 M, 0.8M and 1M NaCl.

VLP Concentration Using Membrane Filter

The HPV 16 L1 or HPV 18 L1 fractions collected from heparin chromatography or cation-exchange chromatography were dialyzed against PBS buffer+0.01% Tween 80 containing NaCl concentration of 0.1-0.325 M. Dialyzed sample was concentrated with amicon ultra YM-50 or YM-100 (Millipore, USA) following the manufacturer's instructions.

SDS-PAGE and Western Blotting

The samples were separated by SDS-PAG electrophoresis (SDS-PAGE) using 12% polyacrylamide gels following Laemmli's method (M. P. McCarthy, W. I. White, F. Palmer-Hill, S. Koenig, J. A. Suzich, *J Virol* 72 (1998) 32-41). For Western blot analysis, HPV 16 L1 or HPV 18 L1 containing samples were transferred from the SDS-PAG to PVDF membrane (Q-Biogene, USA) operated at 200 mA for 120 min. The L1 protein was detected using rabbit anti-HPV 16 L1 or anti-HPV 18 L1 antibody (PIERCE, USA) as the primary antibodies. Goat anti-rabbit IgG-HRP conjugate (PIERCE, USA) was used as the secondary antibody. Bands were visualized using Western blotting luminal reagent (Santa Cruz Biotechnology, USA).

Electron Microscopy

The purified HPV L1 protein was applied onto a carbon-coated grid and negatively stained with 2% phosphotungstic acid. Photomicrographs were taken at a final magnification of 41,000× using transmission electron microscope TEM200CX (S. N. Kim, et al., J. Virol. Methods 139 (2007) 24-30).

Construction of a Pseudovirus

The plasmids for expressing HPV 16 or HPV 18 L1 proteins and L2 proteins, p16SheLL (provided by National Cancer Institute) and p18SheLL (provided by National Cancer Institute), and plasmids carrying the reporter gene pYSEAP (provided by National Cancer Institute) were cotransfected into 293TT cells (provided by National Cancer Institute) using Lipofectamine 2000 (Invitrogen, USA). Transfected 293TT cells were incubated for 72 hrs before disrupting with lysis buffer (PBS+0.5% Brij58, 0.2% Benzonase, 0.2% plasmid-safe ATP-dependent Dnase). The cell debris was precipitated after centrifugation at 12,000 g for 10 min and the clarified cell supernatant was used for neutralization assay.

Mouse Immunization

Six-week-old male Balb/c mice were subcutaneously immunized for 3-times at 3-week intervals. Two µg each of L1 protein purified from heparin chromatography and cation-exchange chromatography were used for the immunization. Freund's complete adjuvant (Sigma) was used for the first administration, followed by two boosts with Freund's incomplete adjuvant (Sigma). Control group was administered with Freund's complete adjuvant and Freund's incomplete adjuvant diluted and mixed in same ratio. Ten days after the second boost, animals were bled through their tail vein, and the pooled sera were used for neutralization assay.

SEAP-Based Neutralization Assay

The 293TT cells were seeded into a 96-well culture plates at $3 \times 10^4$ cells/well and incubated for 4 hrs at 37° C. and 5% $CO_2$. The sera of mice immunized with HPV type 16 and HPV type 18 L1 proteins were serially diluted from 1:100 to 1:10,000,000. Afterwards, the sera were diluted at 1:4 with the HPV type 16 and Type 18 pseudovirus. The diluted serum-pseudovirus mixtures were added to the 293TT cells grown in 96-well plate and incubated for 4 hrs at 37° C. and under 5% $CO_2$. The level of SEAP expression in the medium after 72 hrs of incubation was determined by using p-nitrophyl phosphate disodium salt hexahydrate (Sigma, USA) as a substrate. Neutralization antibody titer was measured by determining the half value of the O.D from the well with 293TT cells infected with pseudovirus alone.

Experiment Results

1. Purification Result of HPV 16 L

Heparin Chromatography

Figure 3:
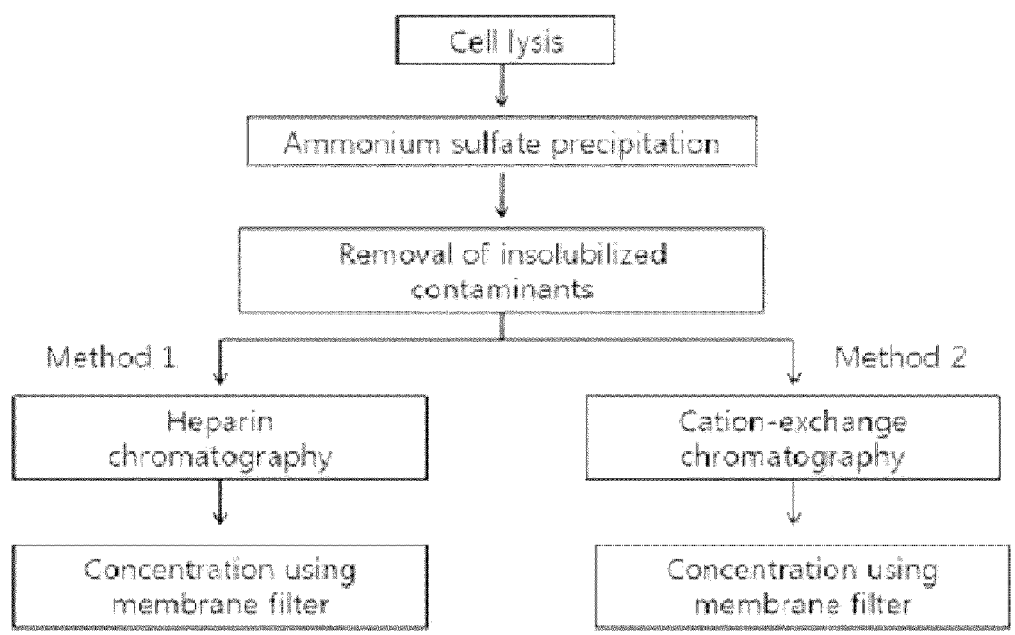
FIG. 3 is a workflow chart showing the experimental procedures used to purify HPV 16 L1 and HPV 18 L1. The samples were precipitated by ammonium sulfate and incubated with low concentration of NaCl to remove insoluble contaminants before isolating with two purification methods. Method 1 is a heparin chromatography and method 2 is a cation-exchange chromatography method.
Figure 4:
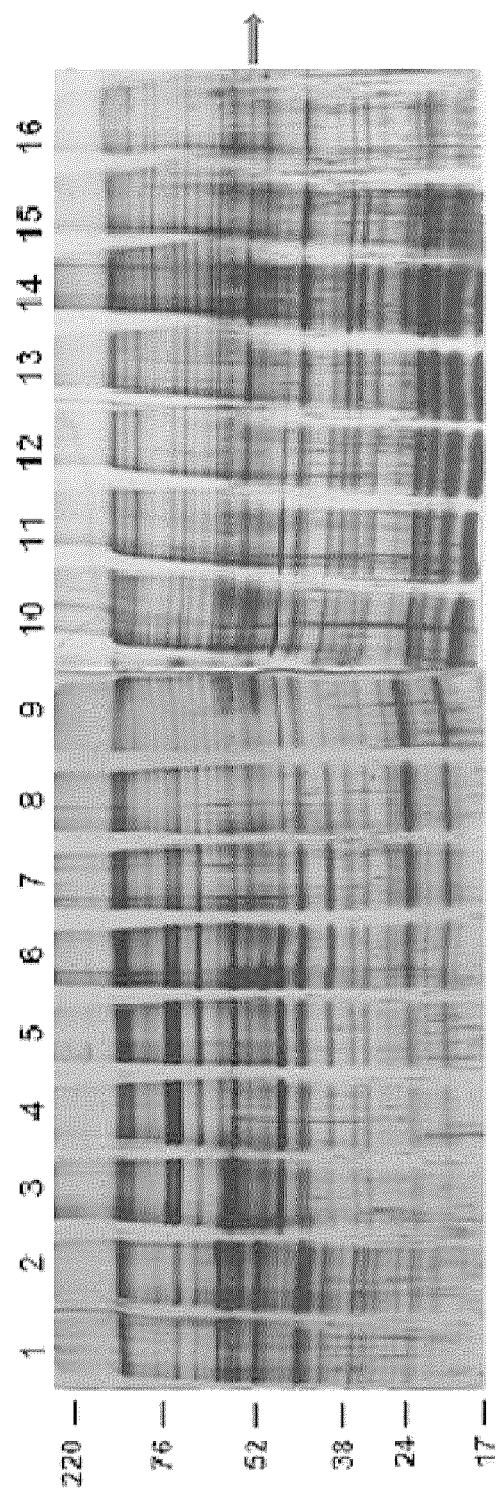
FIG. 4-6 are electrophoretic diagrams showing the purification of HPV 16 L1.
Figure 5:
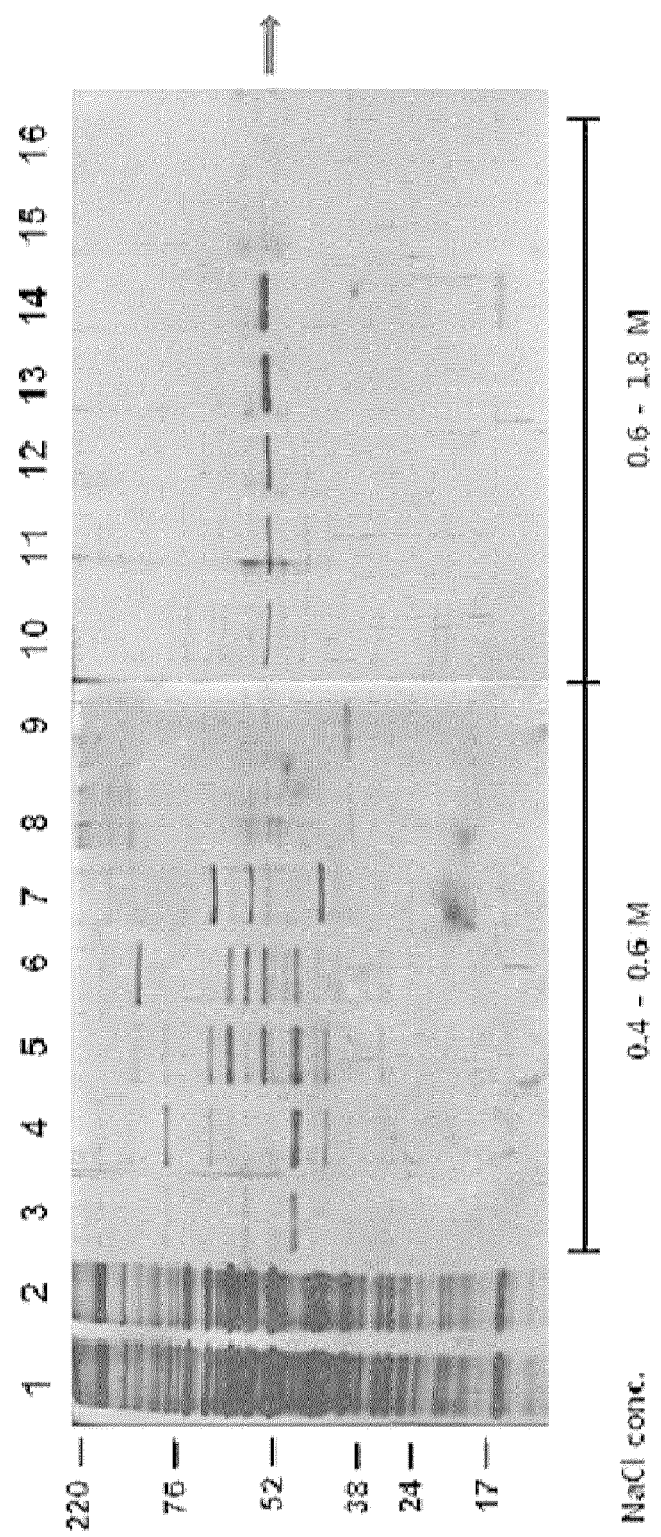
Figure 6:
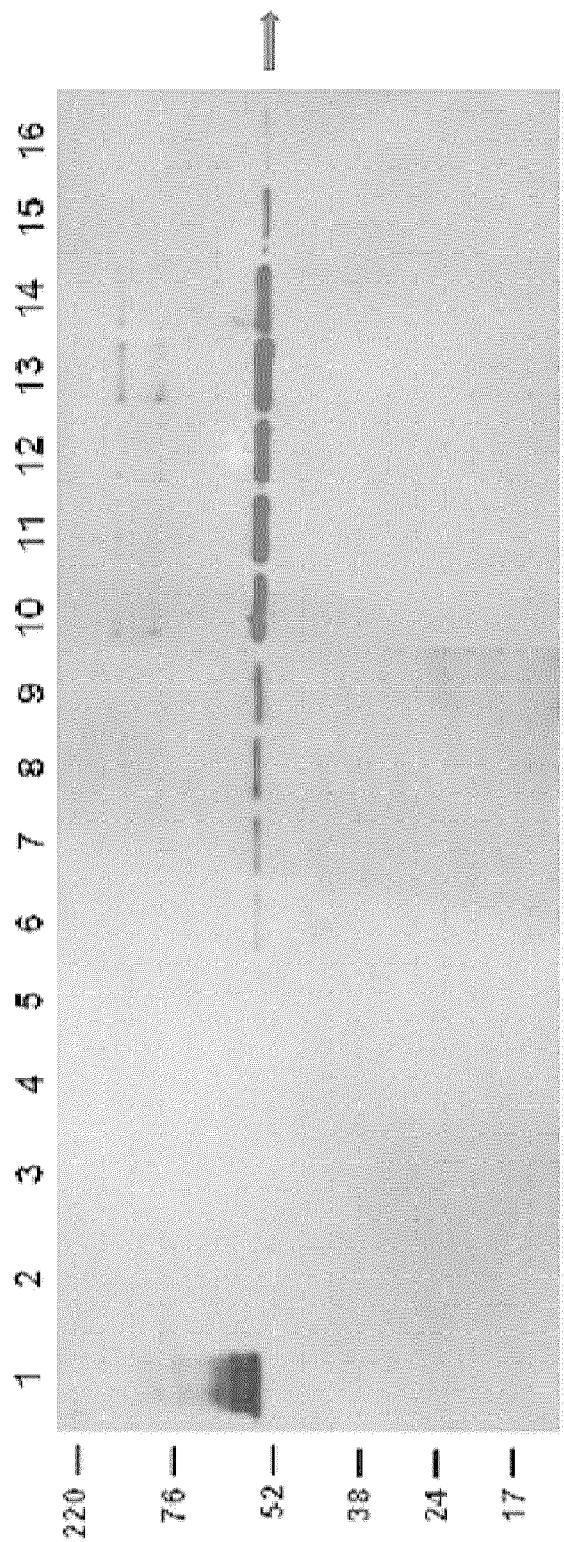

The purification property of heparin chromatography for HPV 16 L1 protein was analyzed. Following is the heparin chromatography result according to Method 1 in FIG. 3. As shown in FIG. 4, without removing the insoluble contaminants through the low concentration of NaCl incubation step, the heparin chromatography result showed high levels of insoluble contaminants. However, when the sample was pretreated with low concentration of NaCl, the heparin chromatography result showed increase in L1 protein purity (FIG. 5). The proteins bound to heparin column were first eluted with a linear gradient of NaCl from 0.325 M to 0.66 M followed by NaCl gradient from 0.66 to 2 M. Most of the contaminants were eluted in the range of 0.325 M to 0.66 M NaCl (FIG. 5) and HPV 16 L1 protein was eluted from NaCl gradient of 0.5 M to 1.3 M (FIG. 6). Result suggests that removing insoluble contaminants by incubating with low concentration of NaCl increased the purity of the L1 protein after heparin chromatography experiment. Loading heparin chromatography column with samples cleared of insoluble contaminants is an effective way of purifying L1 protein.

Cation-Exchange Chromatography

Figure 7:
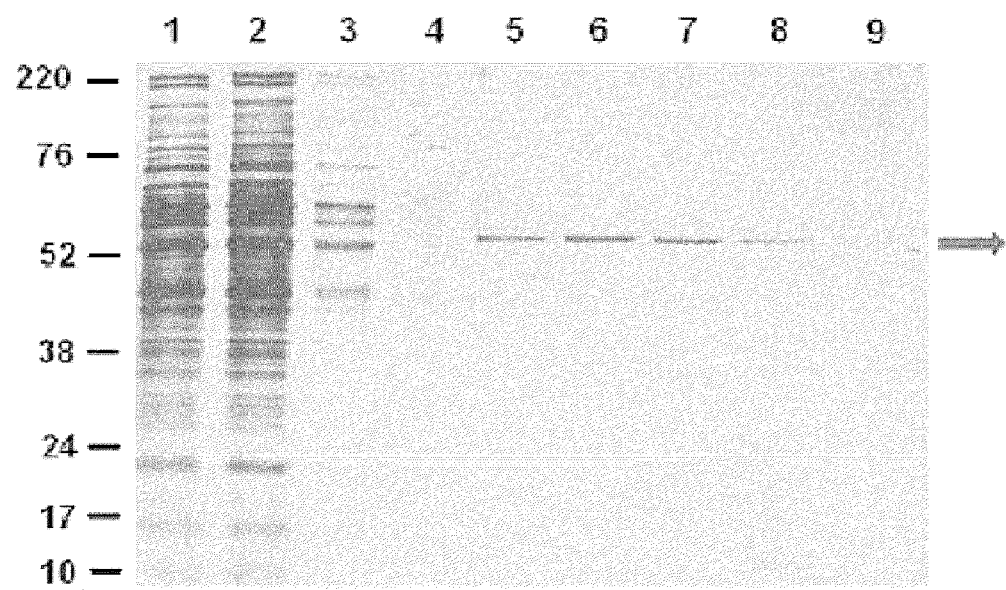
FIG. 7 and FIG. 8 are electrophoretic diagrams showing the purification of HPV 16 L1.
Figure 8:
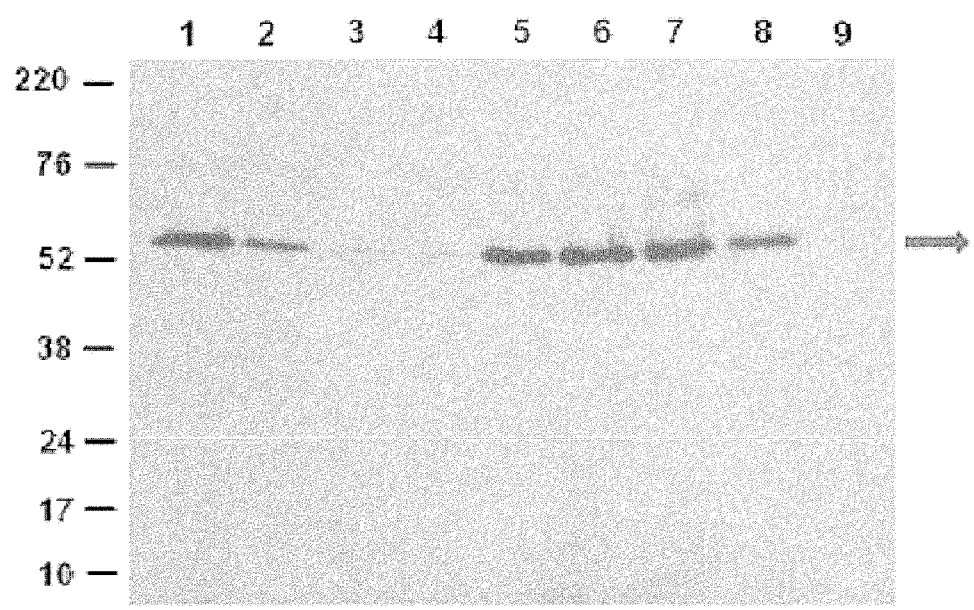

The purification property of cation-exchange chromatography for HPV 16 L1 protein was analyzed. Following is the cation-exchange chromatography result according to Method 2 in FIG. 3. As shown in FIG. 7 and FIG. 8, most of the contaminants were removed by binding to the column resin (FIG. 7). HPV 16 L1 was eluted from NaCl gradient of 0.7 M to 1 M (FIG. 8). Result suggests that removing insoluble contaminants by incubating with low concentration of NaCl increased the purity of the L1 protein through cation-exchange chromatography.

The Purity of the Isolated HPV 16 L1

Figure 9:
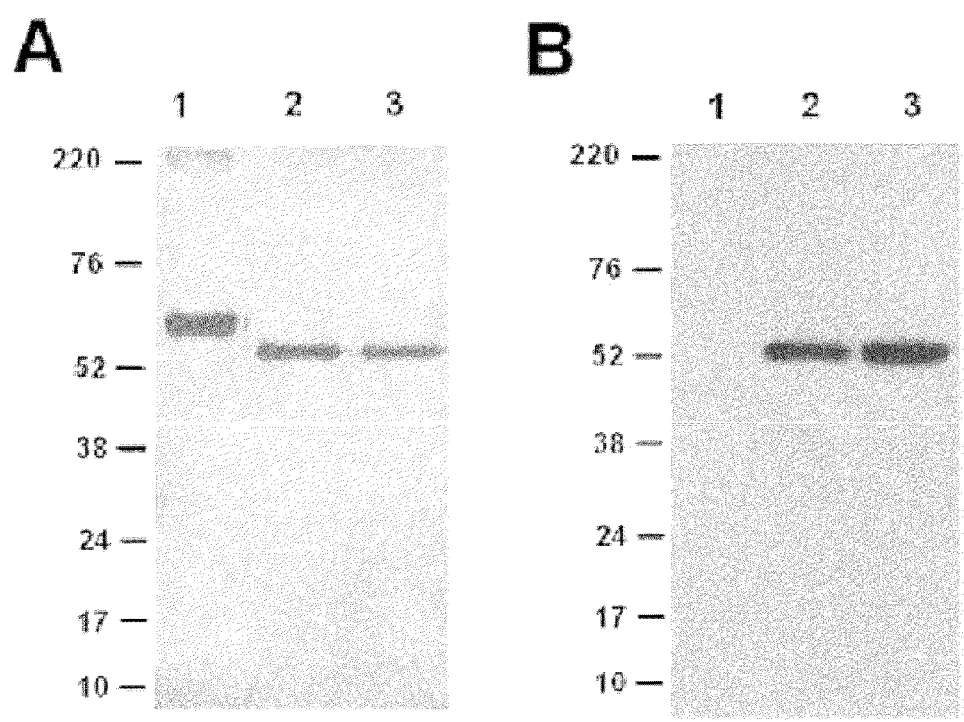
FIG. 9 is electrophoretic diagram showing the purified HPV 16 L1 samples concentrated with membrane filter with cut-off size of 50-100 kDa after pooling the L1 fractions from heparin chromatography and cation-exchange chromatography. Panel A is the SDS-PAGE result and panel B is the Western blotting result. Lane 1, 2, and 3 represents BSA, HPV 16 L1 purified by method 1 and HPV 16 L1 purified by method 2, respectively. Samples were quantified using Bradford assay and each lane was loaded with 200 ng of samples.

The isolated L1 protein fractions were pooled and concentrated with a membrane (YM-50 or YM-100) with cut-off size of 50-100 kDa. As shown in FIG. 9, the purity of L1 protein was almost similar to that of a commercially available BSA standard (purity higher than 96%) (FIG. 9 panel A). The 55 kDa band visible on the SDS-PAGE was detected as a monomer by Western blotting. The BSA band was not visible (FIG. 9 Panel B). This result shows that a highly purified HPV 16 L1 was isolated through this purification process.

Self-Assembly of the Isolated HPV 16 L1 Protein

Figure 10:
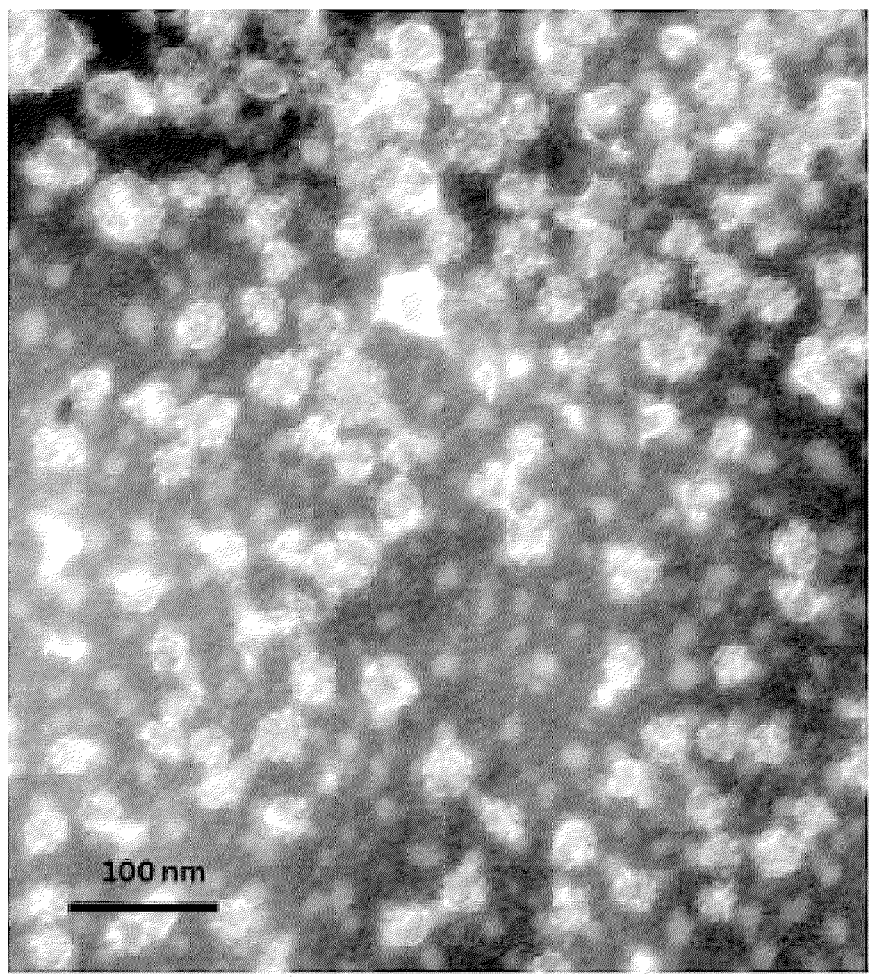
FIG. 10 and FIG. 11 represent electron microscopy images of HPV 16 L1 protein purified according to Method 1 and Method 2 in FIG. 3. The purified HPV 16 L1 protein was applied onto a carbon-coated grid and negatively stained with phosphotungstic acid. Photomicrographs were taken at a final magnification of 41,000× with transmission electron microscope. Scale bar is 100 nm.
Figure 11:
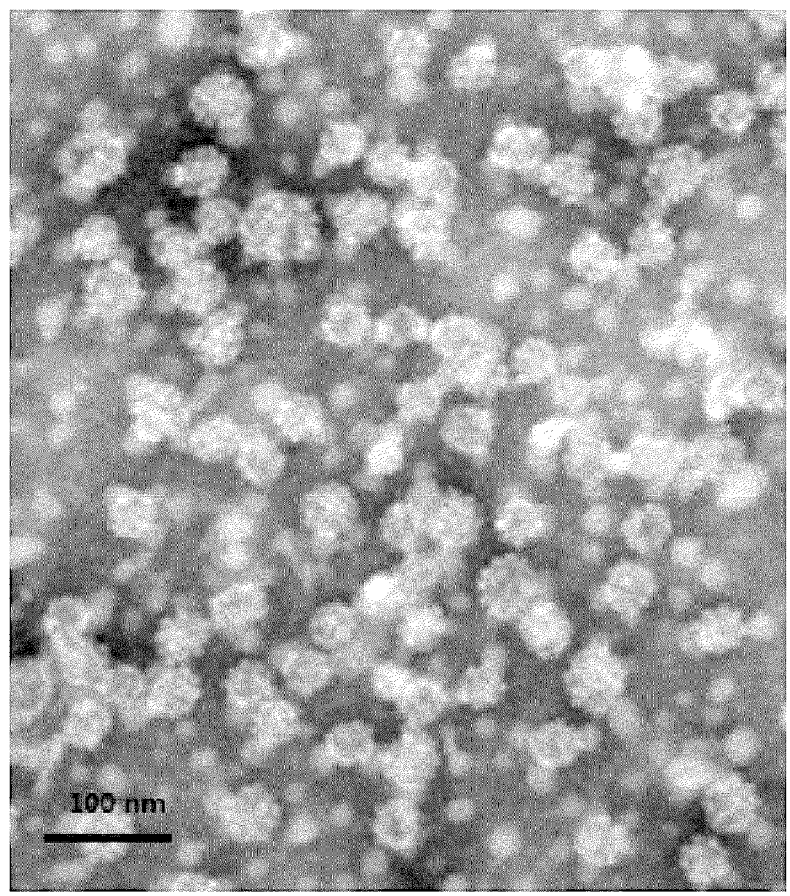

As shown in FIG. 10 and FIG. 11, the HPV 16 L1 protein isolated according to above two procedures self-assembled into VLPs with homogeneous 35 nm or 64 nm (average diameter of 49 nm) particles consistent in shape and size (K. A. Aires, et al., *Appl. Environ.* 368 Microbiol. 72 (2006) 745-752). This result shows that the two purification methods have no effect on the ability of the L1 protein to self-assemble, suggesting that these two purification methods are suitable for purifying HPV 16 L1 protein.

The protein yield for each purification step was analyzed using sandwich ELISA method. An average of 80% debris was removed by cell lysis, ammonium sulfate precipitation and incubation with low concentration of NaCl. The average recovery rate of L1 protein after these steps was 81% (Table 1 and Table 2). The purity of L1 was 0.2% at cell lysis step, but increased up to 0.8-1% after removing contaminants by ammonium sulfate precipitation. The protein purity also increased by 4-5 folds (Table 1 and Table 2).

TABLE 1

| Steps | Total protein (mg) | Total L1 (mg) | Recovery rate (%) | Purity (%) |
|---|---|---|---|---|
| Cell lysate | 3199.7 | 7.9 | 100 | 0.2 |
| Ammonium sulfate precipitation | 1914 | 7.2 | 92 | 0.4 |
| Insoluble protein removal | 642.1 | 6.7 | 84 | 1 |
| Heparin chromatography | 6 | 6.6 | 83 | 109 |
| Membrane filter concentration | 5 | 5 | 64 | 100 |

TABLE 2

| Steps | Total protein (mg) | Total L1 (mg) | Recovery rate (%) | Purity (%) |
|---|---|---|---|---|
| Cell lysate | 3199.7 | 7.9 | 100 | 0.2 |
| Ammonium sulfate precipitation | 1914 | 7.2 | 92 | 0.4 |
| Insoluble protein removal | 713.5 | 5.7 | 72 | 0.8 |
| Cation-exchange chromatography | 5.1 | 4.9 | 62 | 96 |
| Membrane filter concentration | 4.8 | 4.9 | 62 | 101 |

However, the total recovery rate of purified L1 protein from heparin chromatography was 64% (Table 1) and from cation-exchange chromatography was 62% (Table 2). The 64% or 62% are the highest recovery rate to be reported.

2. Purification Result of HPV 18 L1

Heparin Chromatography

Figure 12:
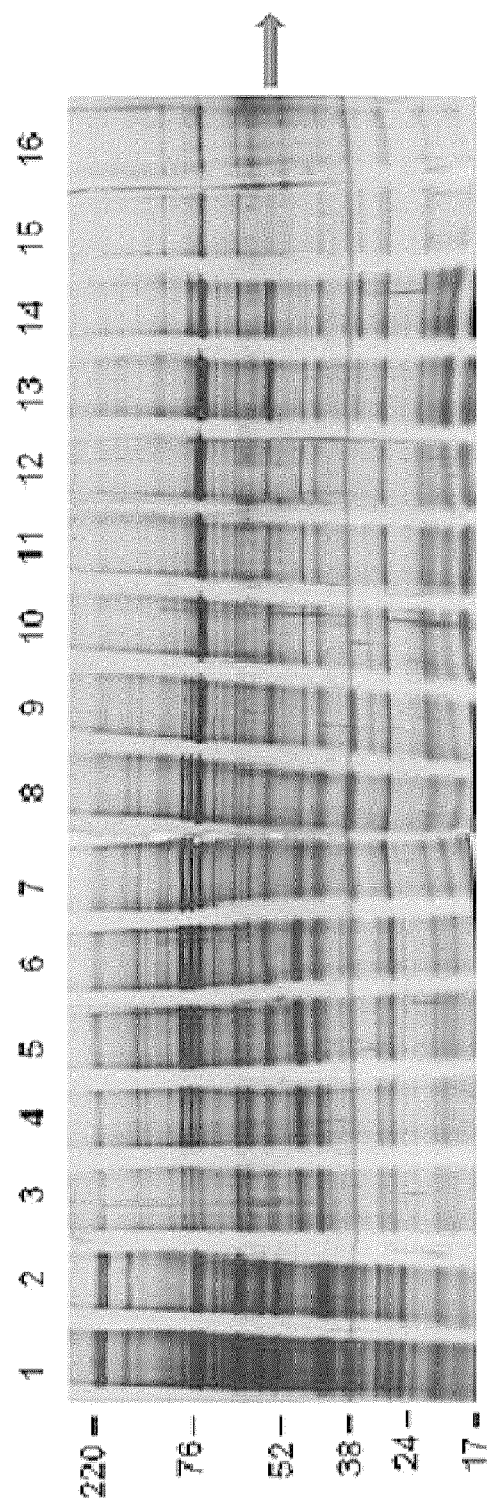
FIGS. 12-14 are electrophoretic diagrams showing the purification of HPV 18 L1.
Figure 13:
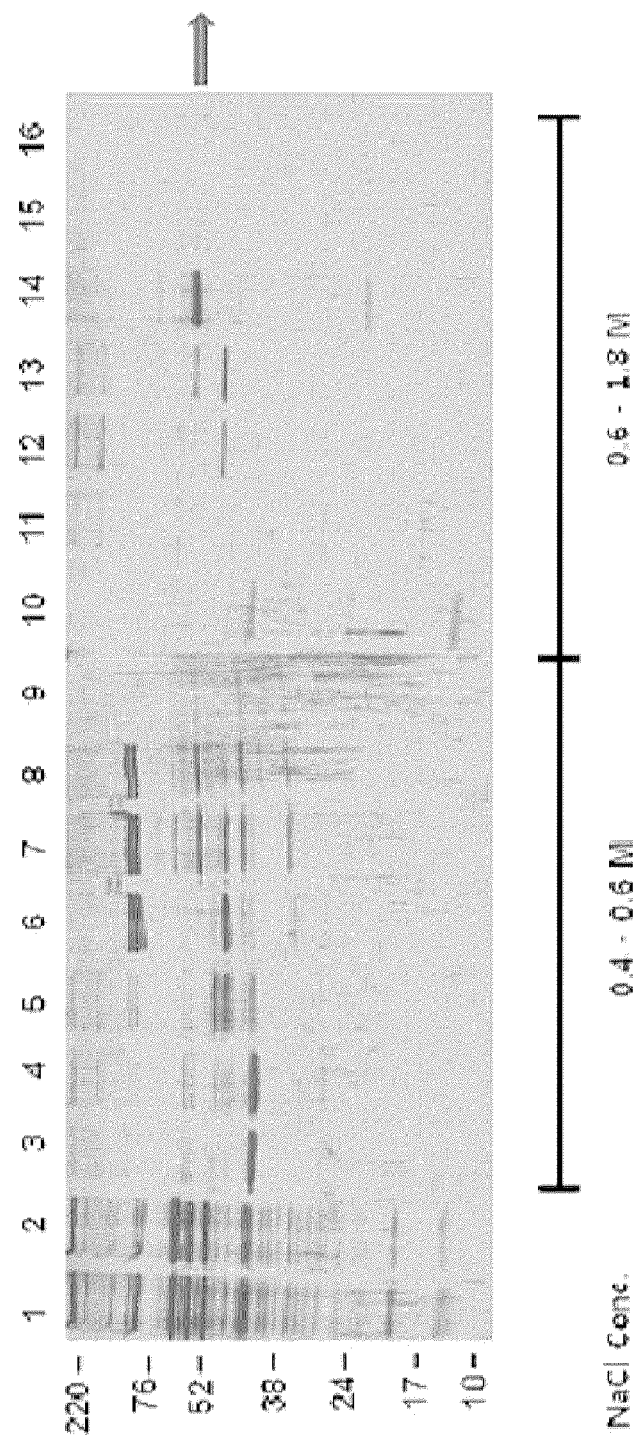
Figure 14:
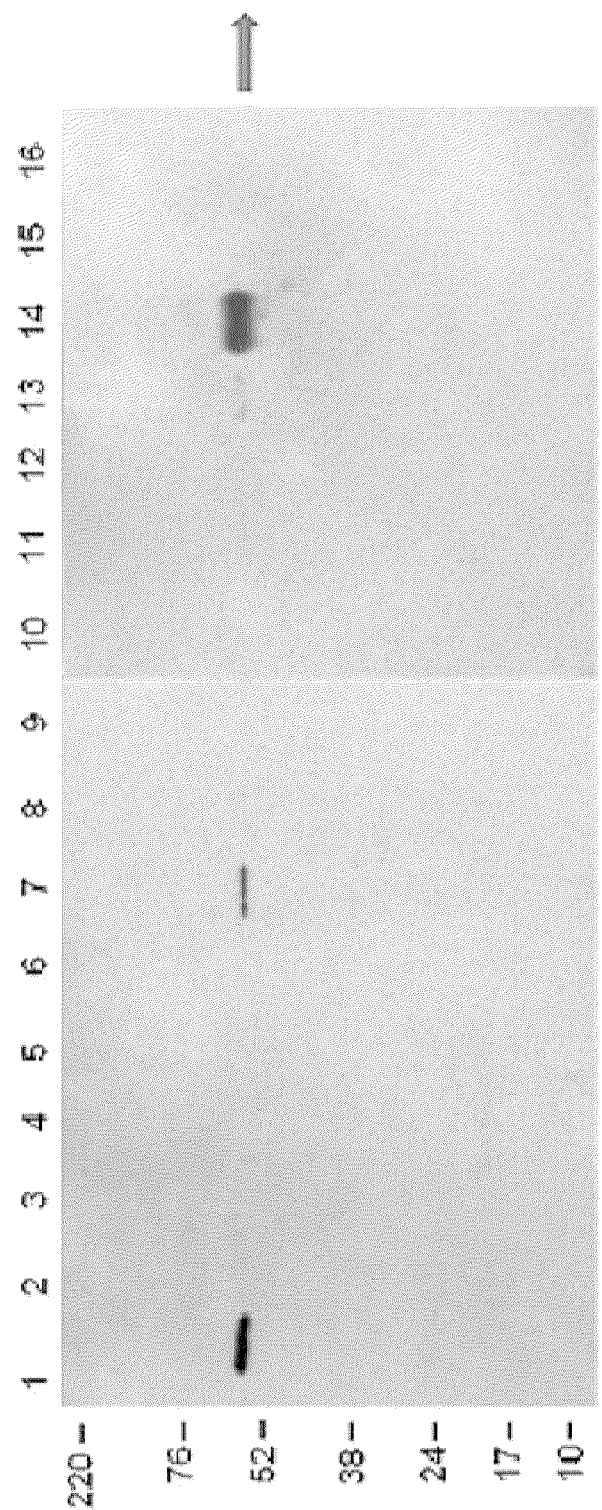

The purification property of heparin chromatography for HPV 18 L1 protein was analyzed. Following is the heparin chromatography result according to Method 1 in FIG. 3. As shown in FIG. 12, without removing the contaminants through the low concentration of NaCl incubation step, the heparin chromatography result showed high level of insoluble contaminants. However, the sample pretreated with low concentration of NaCl, showed increase in the purity of the L1 protein after heparin chromatography experiment (FIG. 13). The proteins bound to heparin column were first eluted with a linear gradient of NaCl from 0.325 M to 0.66 M followed by NaCl gradient from 0.66 to 2 M. Most of the contaminants were eluted in the range of 0.325 M to 0.5 M NaCl (FIG. 13) and HPV 18 L1 protein was eluted from NaCl gradient of 0.5 M to 1.3 M (FIG. 14). The result suggests that in accordance with HPV 16 L1 purification, heparin chromatography is an effective method for purifying HPV 18 L1.

Cation-Exchange Chromatography

Figure 15:
FIG. 15 and FIG. 16 are electrophoretic diagrams showing the purification of HPV 18 L1.
Figure 16:
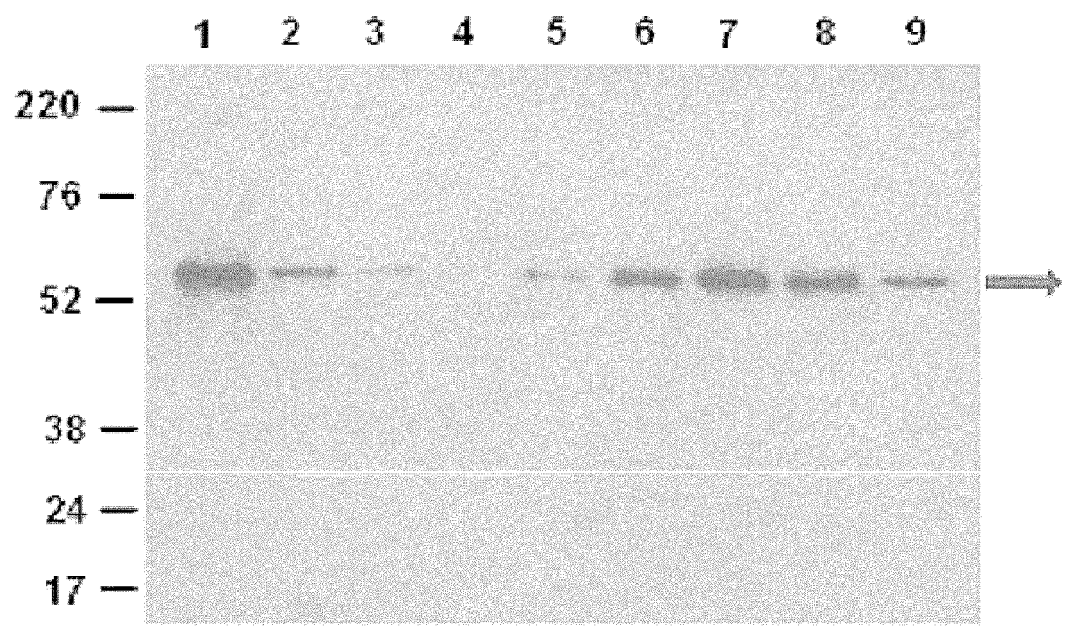

The purification property of cation-exchange chromatography for HPV 18 L1 protein was analyzed. Following is the cation-exchange chromatography result according to Method 2 in FIG. 1c. 1 As shown in FIG. 15, most of the contaminants were removed by binding to the column resin. HPV 18 L1 was eluted at NaCl gradient of 0.8 M to 1 M (FIG. 16). Result suggests that removing insoluble contaminants by incubating with low concentration of NaCl increased the purity of the L1 protein isolated from cation-exchange chromatography.

The Purity of the Isolated HPV 18 L1

Figure 17:
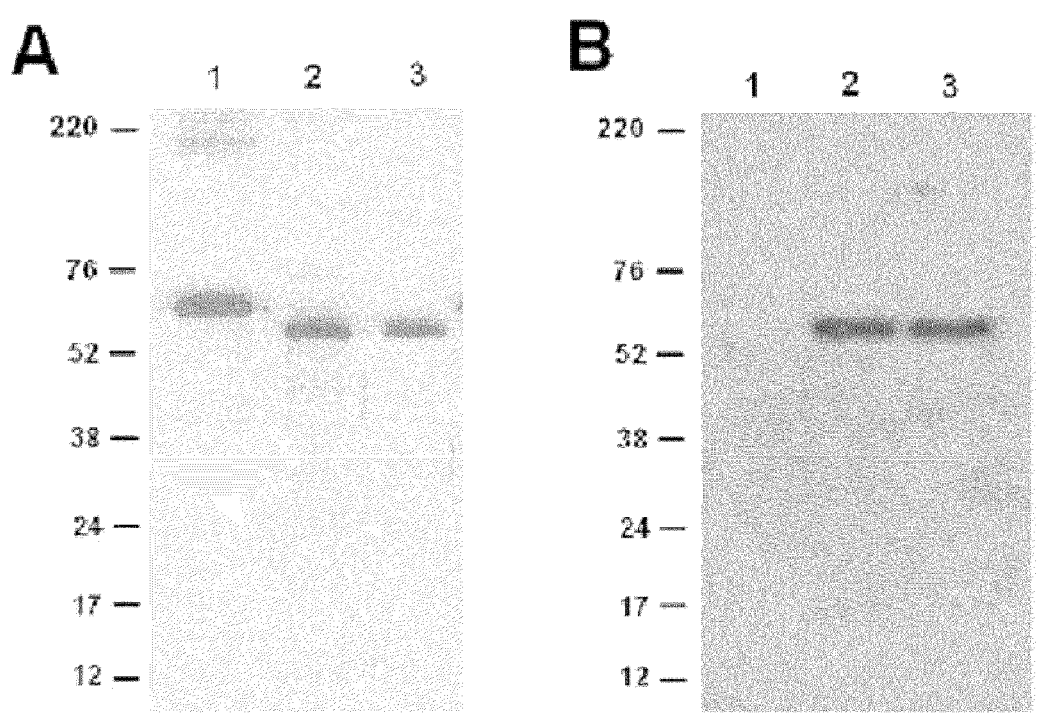
FIG. 17 is electrophoretic diagram showing the purified HPV 18 L1 samples concentrated with membrane filter with cut-off size of 50-100 kDa after pooling the L1 fractions from heparin chromatography and cation-exchange chromatography. Panel A is the SDS-PAGE result and panel B is the Western blotting result. Lane 1, 2, and 3 represents BSA, HPV 18 L1 purified by method 1 and HPV 18 L1 purified by method 2, respectively. Samples were quantified using Bradford assay and each lane was loaded with 200 ng of samples.
Figure 18:
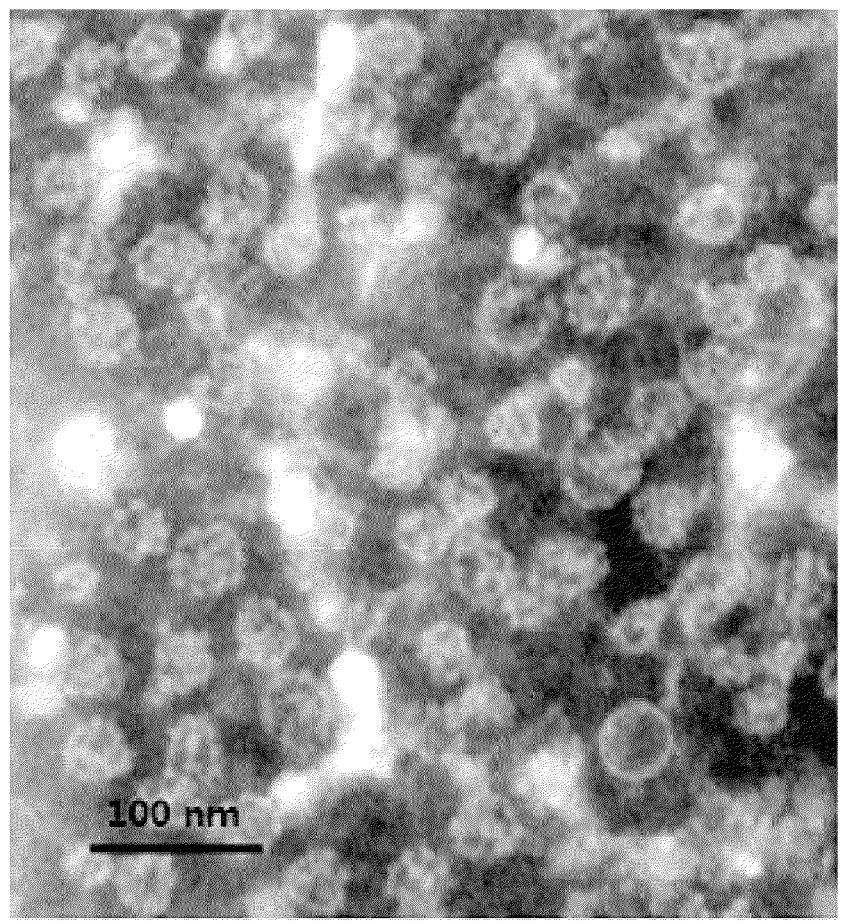
FIG. 18 and FIG. 19 represent electron microscopy images of HPV 18 L1 protein purified according to Method 1 and Method 2 in FIG. 3. The purified HPV L1 protein was applied onto a carbon-coated grid and negatively stained with phosphotungstic acid. Photomicrographs were taken at a final magnification of 41,000× with transmission electron microscope. Scale bar is 100 nm.

The isolated L1 protein fractions were pooled and concentrated with a membrane (YM-50 or YM-100) with cut-off size of 50-100 kDa. As shown in FIG. 17, the purity of L1 protein was almost similar to that of a commercially available BSA standard (purity higher than 96%) (FIG. 17 panel A). The 55 kDa band visible on the SDS-PAGE was detected as a monomer by Western blotting. The BSA band was not visible (FIG. 18 Panel B). This result shows that a highly purified HPV 18 L1 was isolated by above two purification procedures.

Self-Assembly of the Isolated HPV 18 L1 Protein

Figure 19:
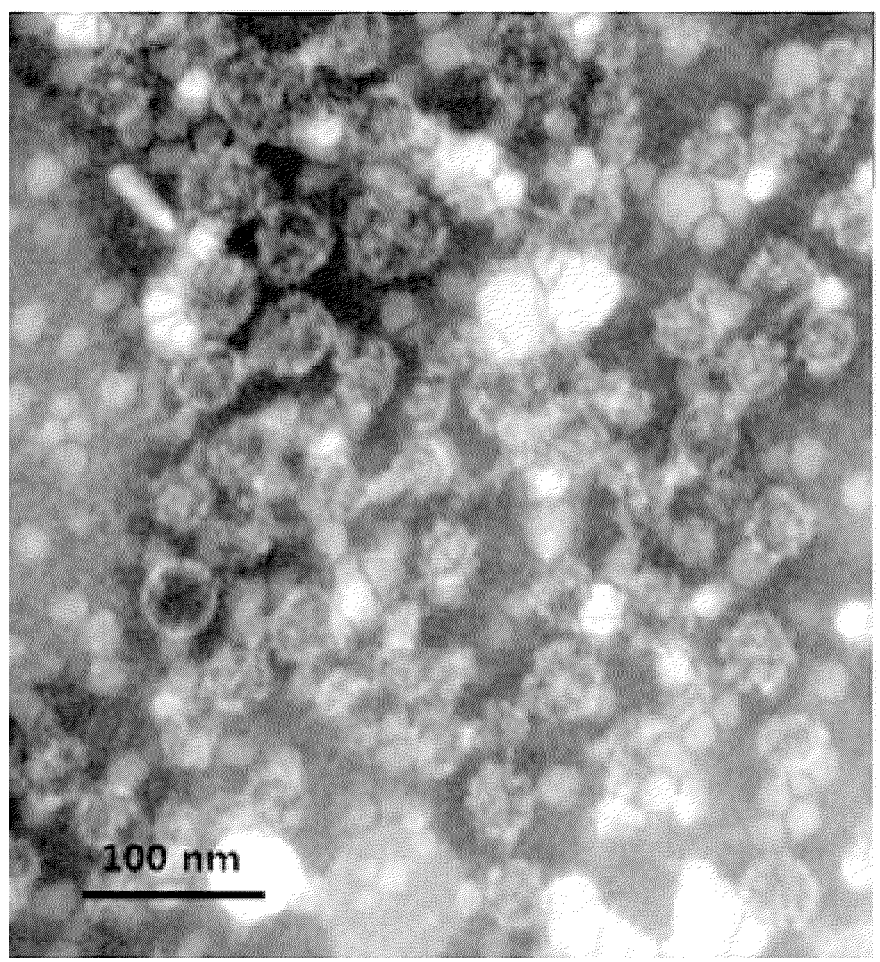

As shown in FIG. 18 and FIG. 19, the HPV 18 L1 protein isolated according to above two procedures self-assembled into VLPs with homogeneous 35 nm or 64 nm (average diameter of 49 nm) particles consistent in shape and size (K. A. Aires, et al., *Appl. Environ.* 368 Microbiol. 72 (2006) 745-752). This result shows that the two purification methods have no effect on the ability of the L1 protein to self-assemble, suggesting these two purification methods are suitable for purifying HPV 18 L1 protein.

In summary, the experiment provided evidence for a purification method with higher purity and higher recovery rate for isolating HPV 16 L1 and HPV 18 L1 proteins. This purification method has less complicated steps and are less time consuming than other purification methods, such as sucrose cushion or size-exclusion chromatography methods.

3. Neutralization Assays of Purified HPV Type 16 and Type 18 L1 Protein

Figure 20:
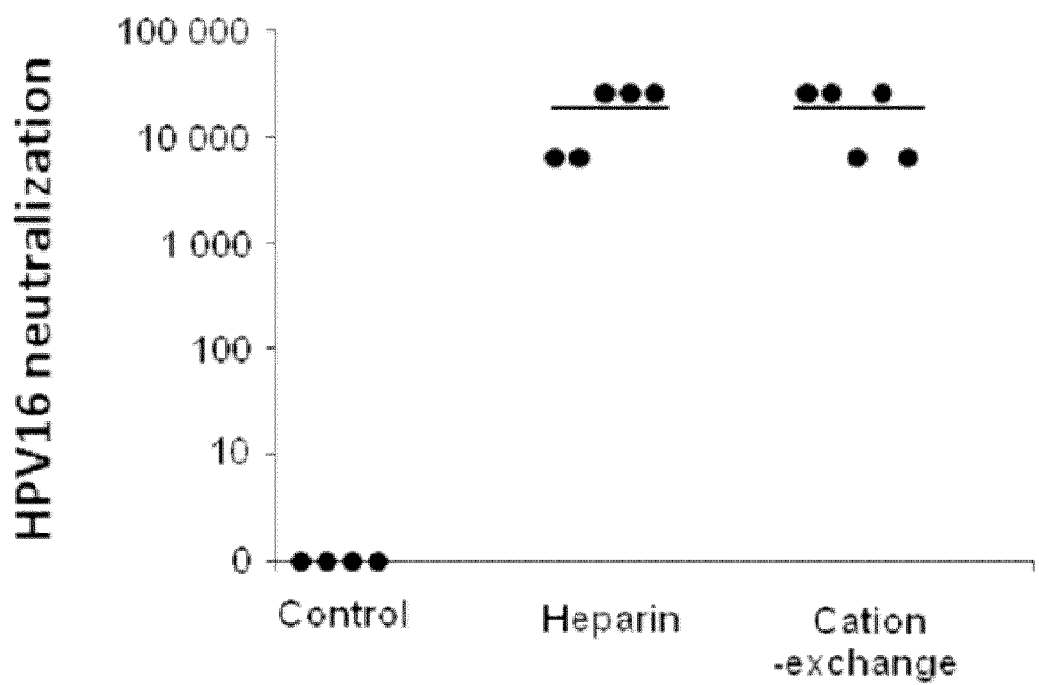
FIG. 20 and FIG. 21 are graphs showing neutralization of purified HPV 16 and 18 L1 each purified by heparin chromatography and cation-exchange chromatography. Purified L1 protein was immunized for 3-times at 3-week intervals. The neutralization antibody titer in serum was measured by SEAP-based neutralization assay. In X axis, control is group immunized with adjuvant only; heparin is group immunized with L1 protein purified by heparin chromatography; and cation-exchange is group immunized with L1 protein purified by cation-exchange chromatography. Y axis is the serum dilution factors.
Figure 21:
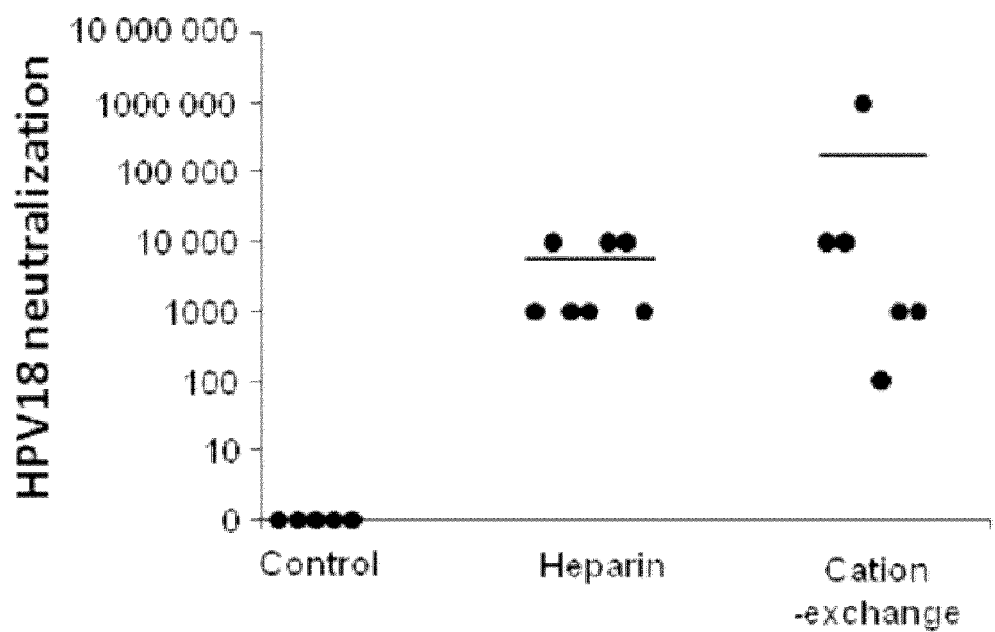

Mice were immunized with the purified HPV type 16 and type 18 L1 proteins to test the neutralizing antibody titer. Neutralizing antibody was induced at average of 1:18,000 dilution of HPV type 16 L1 purified by heparin chromatography and cation-exchange chromatography (FIG. 20). In the case of HPV type 18 L1, neutralizing antibody was developed at average of 1:5,000 dilution for L1 purified by heparin chromatography and average of 1:170,000 dilution for L1 purified by cation-exchange chromatography (FIG. 21). This results shows that the purified HPV type 16 and type 18 L1 proteins can induce high levels of neutralizing antibodies.

Example 2

Manufacturing a Very Short Lipopolysaccharide (LPS) Adjuvant CIA05

The inventors screened a strain (*E. coli* EG0021) having a very short sugar chain of lipopolysaccharide from *Escherichia coli* living in the bowls of healthy humans and deposited the strain *E. coli* EG0021 to the Korean Culture Center of Microorganisms (KCCM) on May 2, 2002, its accession number KCCM 10374 (c.f., Republic of Korea Pat. No. 0456681; WO 2004/039413; Korean Pat. No. 0740237; WO 2006/121232). Purification of LPS from this strain was done according to the methods disclosed in Korean Pat. No. 0456681; WO 2004/039413; Korean Pat. No. 0740237; and WO 2006/121232. The molecular weight of the LPS was 3,500 Da estimated by MALDI-MASS (Shimadz, Axima-LNR V 2.3.5 (Mode Liner, Power: 106)). The toxicity of the purified LPS was removed by following the protocols disclosed in Korean Pat. No. 0456681; WO 2004/039413; Korean Pat. No. 0740237; and WO 2006/121232. The purified *E. coil* lipopolysaccharide was adjusted to a concentration of 3 mg/ml, and 0.2 N NaOH was mixed with the lipopolysaccharide at a mixing ratio of 1:1 (by volume), deacylated for 140 minutes while shaking at 60° C. every 10 minute. 1 N acetic acid at a volume about ⅕ of the initial 0.2 N NaOH were added to titrate the pH to 7.0. After titration, the resulting mixture was precipitated by ethanol to obtain non-toxic lipopolysaccharide (CIA05).

Example 3

Figure 22:
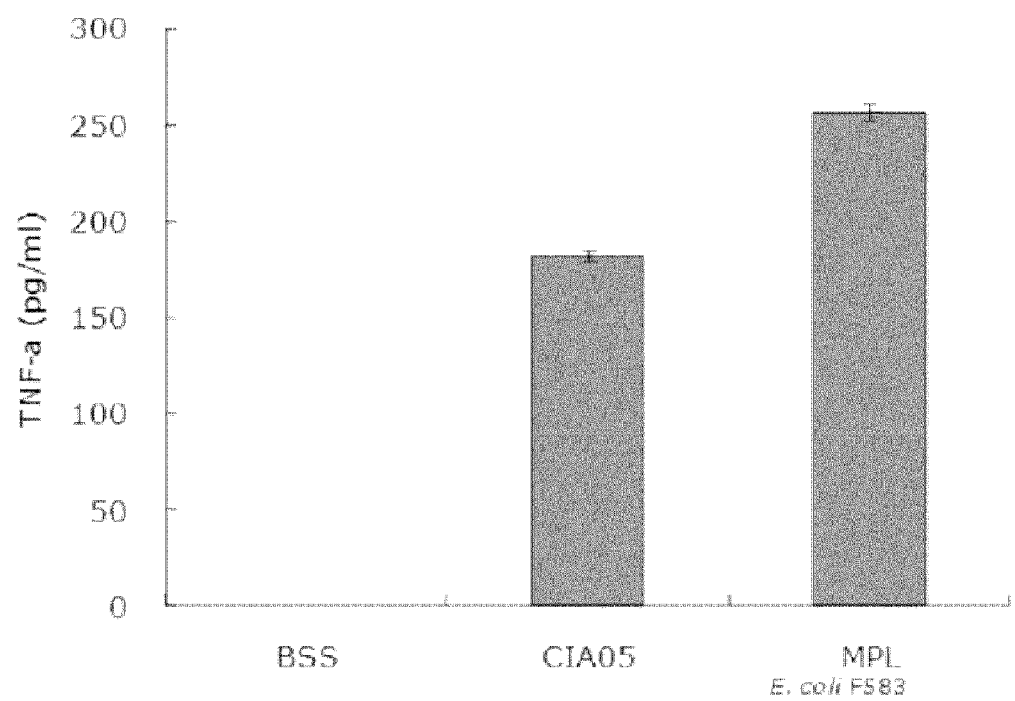
FIG. 22 is a graph showing that the novel adjuvant CIA05 has less toxicity than MPL.

Comparing the Toxicity of the Novel Adjuvant CIA05 with Conventional Adjuvant MPL The novel adjuvant CIA05 developed in this invention to be used for vaccinating cervical cancer were compared with the conventional MPL (Monophosphoryl lipid A) for its toxicity. Human PBMC (Peripheral Blood Mononuclear Cell) from healthy males donors were seeded at $5 \times 10^5$ cell/ml in a 24-well tissue culture plate. One ml of the growth medium, RPMI 1640+10% FBS was added to each well. The mixture was treated with 1) negative control: BSS (Balanced salt solution) 100 µl; 2) deacylated non-toxic LOS (CIA05) 10 ug/100 ul; 3) MPL (E. coli F583 MPL) 10 ug/100 ul. The treated medium were pooled after 12 hrs, centrifuged and the level of TNF-α secreted by THP-1 (Acute monocytic leukemia) was quantified using ELISA kit (R&D system, DY210). As shown in FIG. 22, CIA05 showed ⅓ lesser toxicity compared to the conventional adjuvant, MPL.

Example 4

Efficacy of the Cervical Cancer Vaccine

Immunization of the Mouse

The purified protein antigen and novel adjuvant CIA05 were administered to mice to induce an immune response. Six-week old female Balb/c mice (SLC, Japan) were randomly selected and grouped into 5 mice. The mice were intramuscularly immunized for 3-times at 2-week intervals with CIA05 alone, Alum (aluminum hydroxide; Brenntag, Germany) alone or mixture of both compounds, with HPV16 L1 VLP 2 µg (FIGS. 23-25), HPV16/18 L1 VLP 1 µg or 4 µg (each type 0.5 µg or 2 µg) (FIGS. 26-30). The control mice were injected with PBS. For comparison, commercially available Cervarix™ and Gardasil™ were administered to the mice at ¹⁄₁₀ of the human dosage. Five weeks after the third injection, blood sera were collected to determine the anti-L1 VLP IgG titer using end-point ELISA method.
Analyzing Immunogenicity Using End-Point ELISA (Analyzing IgG Titer)

Nalge Nunc 96 well microplate (Nalge Nunc International) was coated with 100 µl of coating buffer (50 mM carbonate, pH 9.6, 4° C.) with 0.5 µg/ml of the purified HPV type 16 or type 18 VLP L1 antigen diluted in the buffer. Incubation was overnight at 4° C. Each well was washed three times with washing buffer (PBS, 0.05% Tween 20) and blocked with 300 µl of blocking buffer (PBS with 1% BSA) for 1 hr at 37° C. Mouse sera were 1:2 serially diluted and were added to the coated microplate at 100 µl per well. The plates were incubated for 2 hrs at 37° C. After the reaction, plates were washed two times with washing buffer then 100 µl HRP (horse radish peroxidase) labeled goat anti-mouse IgG (Zymed, 81-6520), goat anti-mouse IgG1 (Serotec, STAR81P) or goat anti-mouse IgG2a (Serotec, STAR82P) were added to the microplate. The plates were incubated for 2 hrs at 37° C. Plates were washed two times with washing buffer and subsequently incubated with 100 µl of HRP substrate TMB (tetramethylbenzidine, BD Bio Science, 55555214) for color development. The reaction was carried out at room temperature for 10 min, and stopped with 100 µl of 1 N $H_2SO_4$. Absorbance (concentration) was read with a microplate reader (BioTek, USA) at 450 nm. The cut-off value of the end point titer was 0.1, determined as the highest serum dilution causing 2-fold absorbance increase in unimmunized serum and shown as mean±SD.

Figure 23:
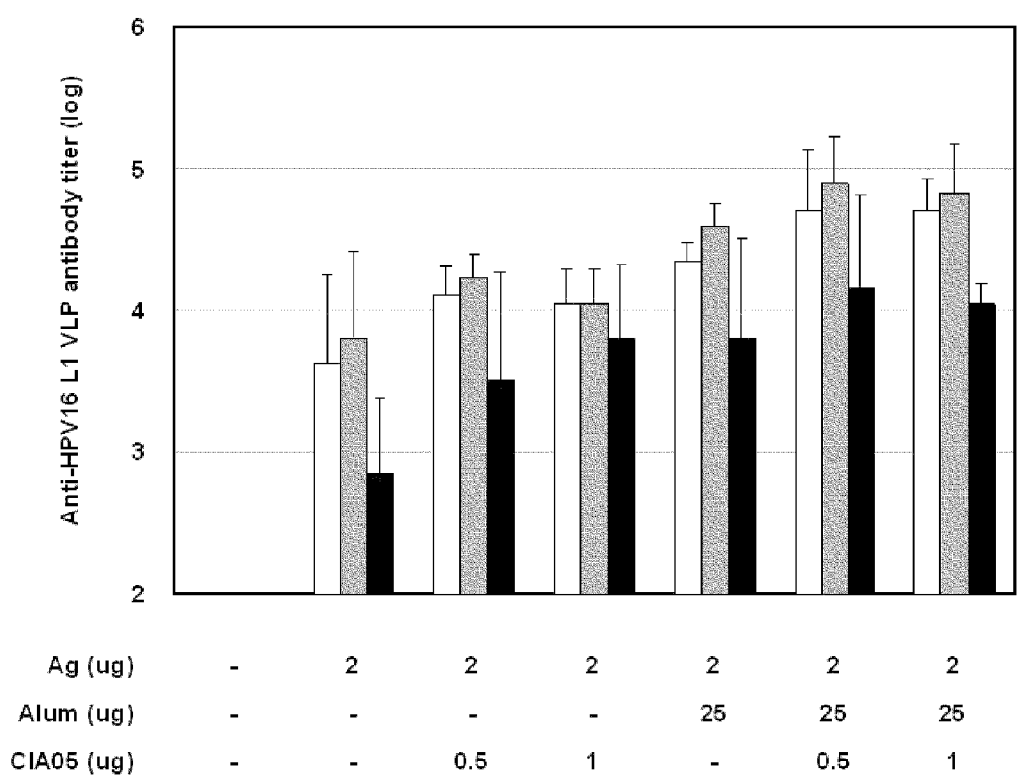
Figure 24:
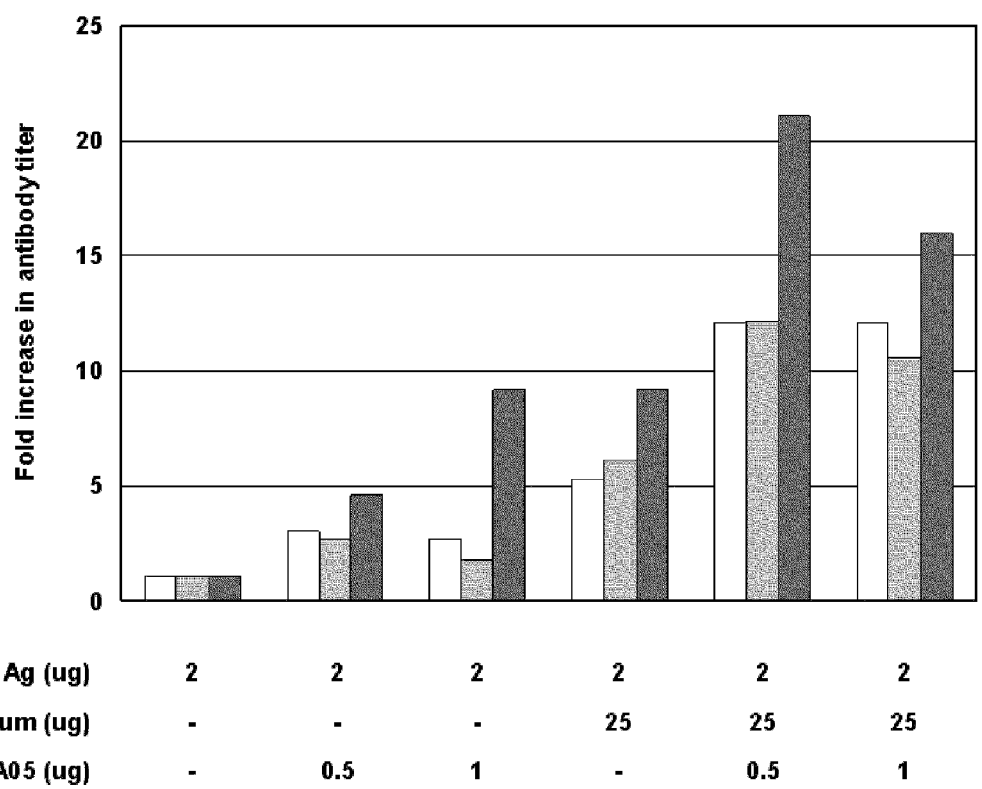

As shown in FIG. 23 and FIG. 24, the antibody titers of IgG, IgG1 and IgG2a increased dramatically when CIA05 was combined with HPV16 L1 VLP antigen. The fold increase of the titer in FIG. 12b clearly represents the pattern of this increase. The CIA05 had a higher immune stimulating effect compared to alum. Therefore, a successful immunization against HPV can be achieved with the basic compositions of the vaccine in this invention, HPV L1 HPV antigen and CIA05.

Figure 25:
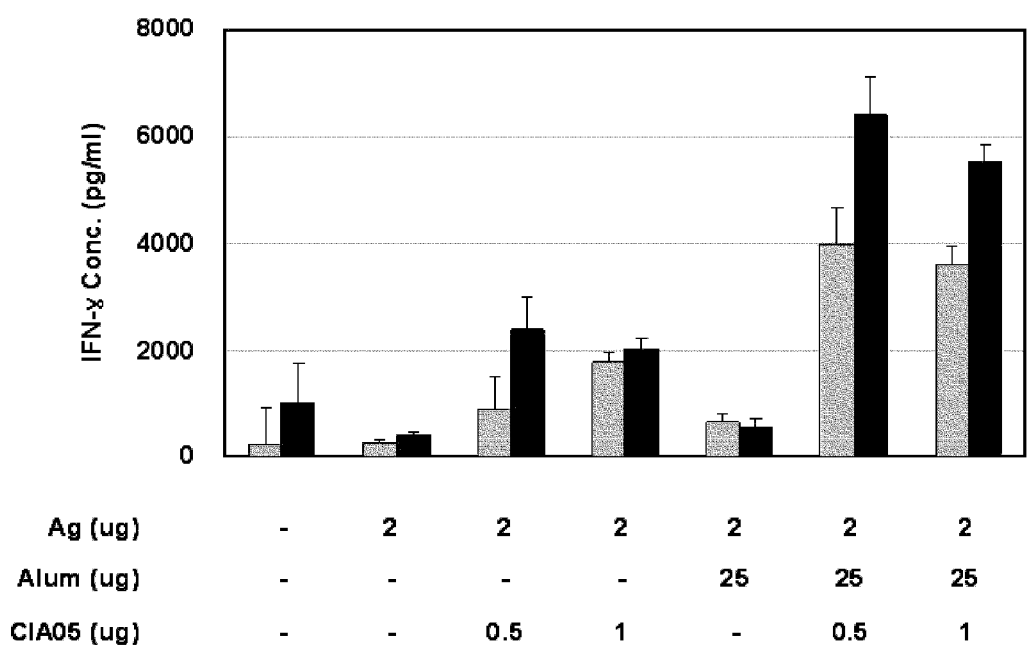
FIG. 25 is a graph showing the excretion level of INF-γ from spleen cells depending on the various concentrations of novel CIA05, HPV 16 L1 VLP and aluminum peroxide (Alum) in the combination mixture. Diagonal lined bar is sample treated with HPV 16 L1 VLP for 2 days; close bar is sample treated with HPV 16 L1 VLP for 3 days.
Figure 26:
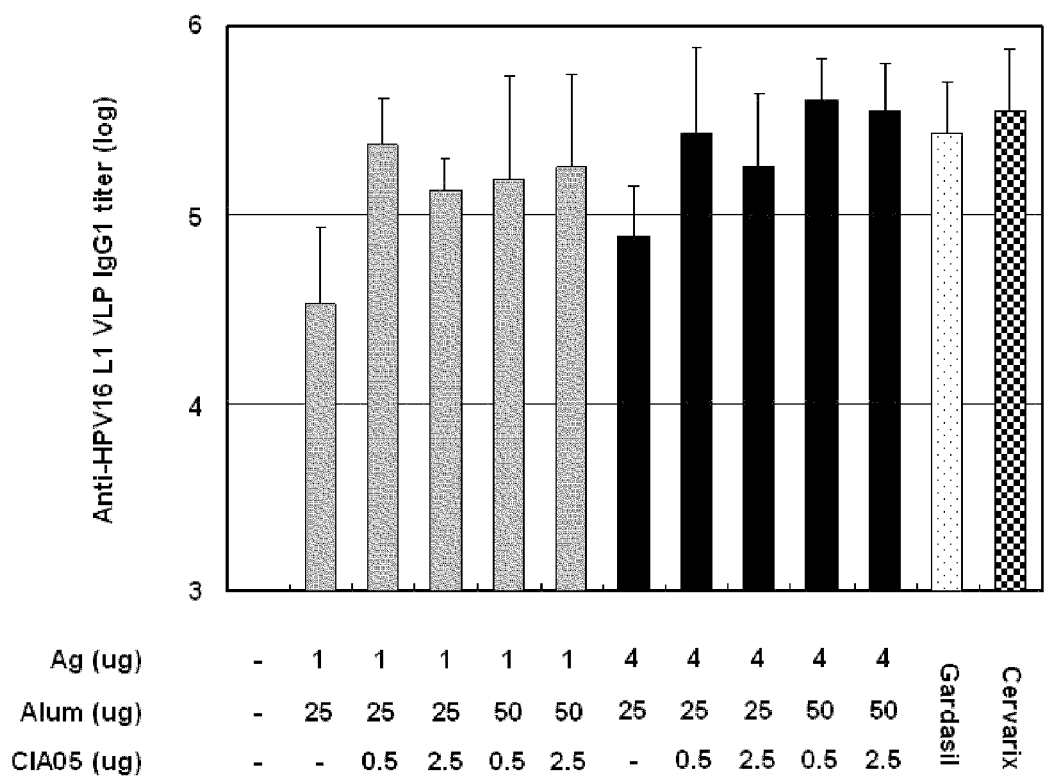
FIG. 26 and FIG. 27 are a graph showing the analysis of total IgG titer depending on the various concentrations of novel CIA05, HPV 16/18 L1 VLP and aluminum peroxide (Alum) in the combination mixture.

In addition, as shown in FIG. 25 and FIG. 26, the total HPV16/18 L1 VLP specific IgG titer was higher when the adjuvant CIA05 and Alum were administered together than Alum administered alone. The IgG titer was significantly higher than Cervarix™ and Gardasil™ treated groups.

Figure 27:
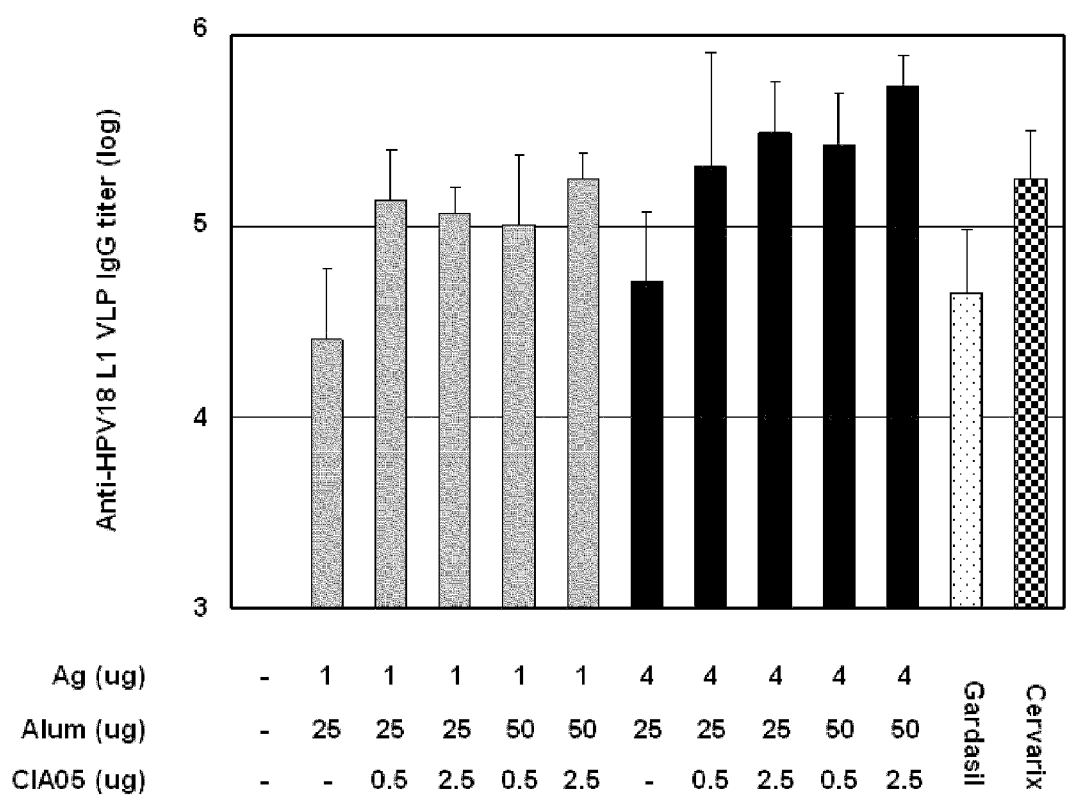
Figure 28:
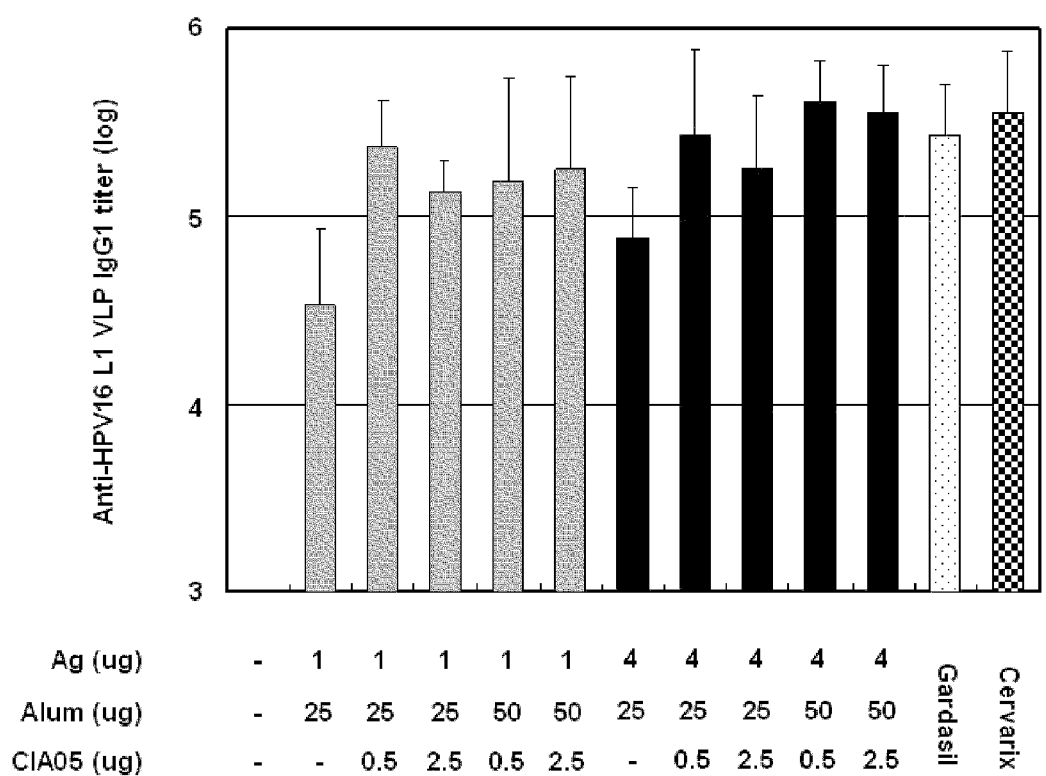
FIG. 28 and FIG. 29 are a graph showing the analysis of IgG1 titer (FIG. 28) and IgG2a titer (FIG. 29) from sera against HPV 16 L1 VLP depending on the various concentrations of novel CIA05, HPV 16/18 L1 VLP and aluminum peroxide (Alum) in the combination mixture.
Figure 29:
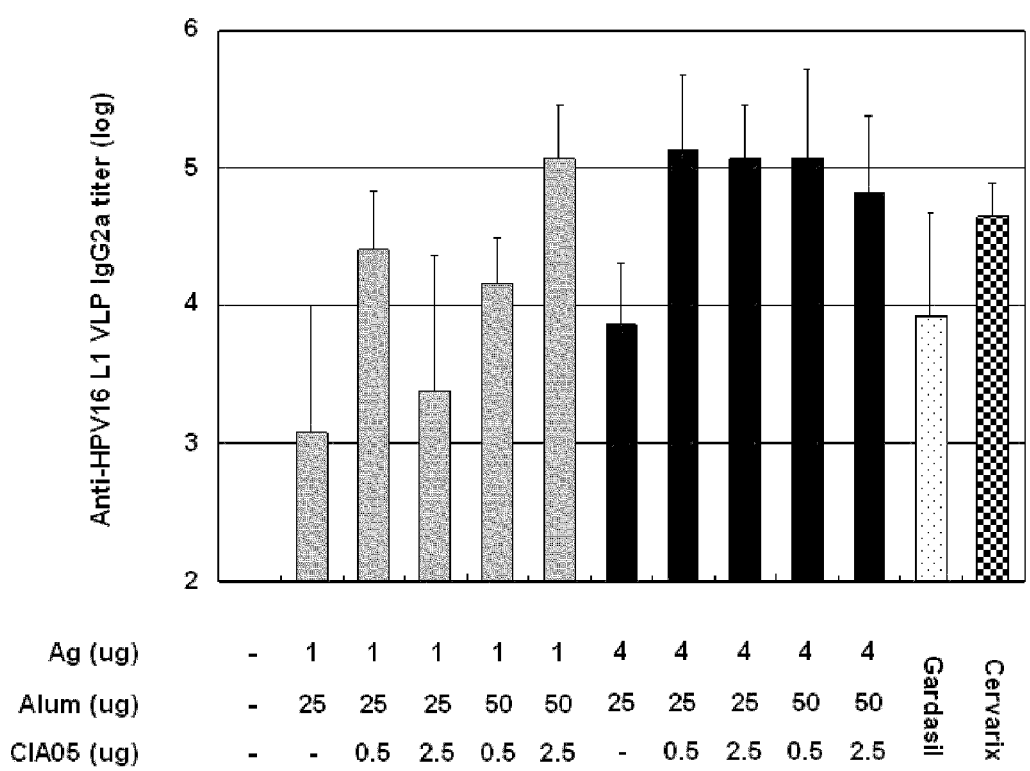

When IgG subtypes were used for titering, as shown in FIG. 27 and FIG. 28, HPV 16 L1 VLP specific IgG1 titer was higher when the adjuvant CIA05 and Alum were administered together than Alum administered alone. The IgG1 titer higher than Cervarix™ and Gardasil™ treated groups (FIG. 27). In the case of IgG2, IgG2 titer was higher when adjuvant CIA05 and Alum were administered together than Alum administered alone. The IgG2 titer was significantly higher than Cervarix™ and Gardasil™ treated groups (FIG. 28).
Analysis of INF-γ Levels Using Mouse Spleen Cells Spleen from the immunized mice were removed aseptically and washed with PBS. Ten holes were punctured on the spleen using a 5 ml syringe in the medium (50 µM β-mercaptoethanol, 1 M HEPES buffer, 10% FBS, 1× RPMI1640 with antibiotics). Spleen cells were disrupted by passing the cell suspension in and out of the syringe. These suspensions were centrifuged at 1500 rpm for 10 min at 4° C. The supernatant was removed and the cell pellets were resuspended with RPMI1640 medium with 10% FBS, 100 µg/ml streptomycin and 50 mM β-mercaptoethanol). Spleen cells were dispensed in each well and HPV16 L1 VLP was added at 15 µg/ml of concentration and incubated for 48-72 hrs at 37° C. The INF-γ levels excreted from mouse spleen cells were determined using ELISA kit (BD OptEIA mouse ELISA kit).

As shown in FIG. 25, adding CIA05 with HPV16 L1 greatly increased the INF-γ levels, and CIA05 showed higher immune stimulating effect when compared with alum. Therefore, a successful immunization against HPV can be achieved with the basic compositions of the vaccine in this invention, HPV L1 VLP antigen and CIA05.

Figure 30:
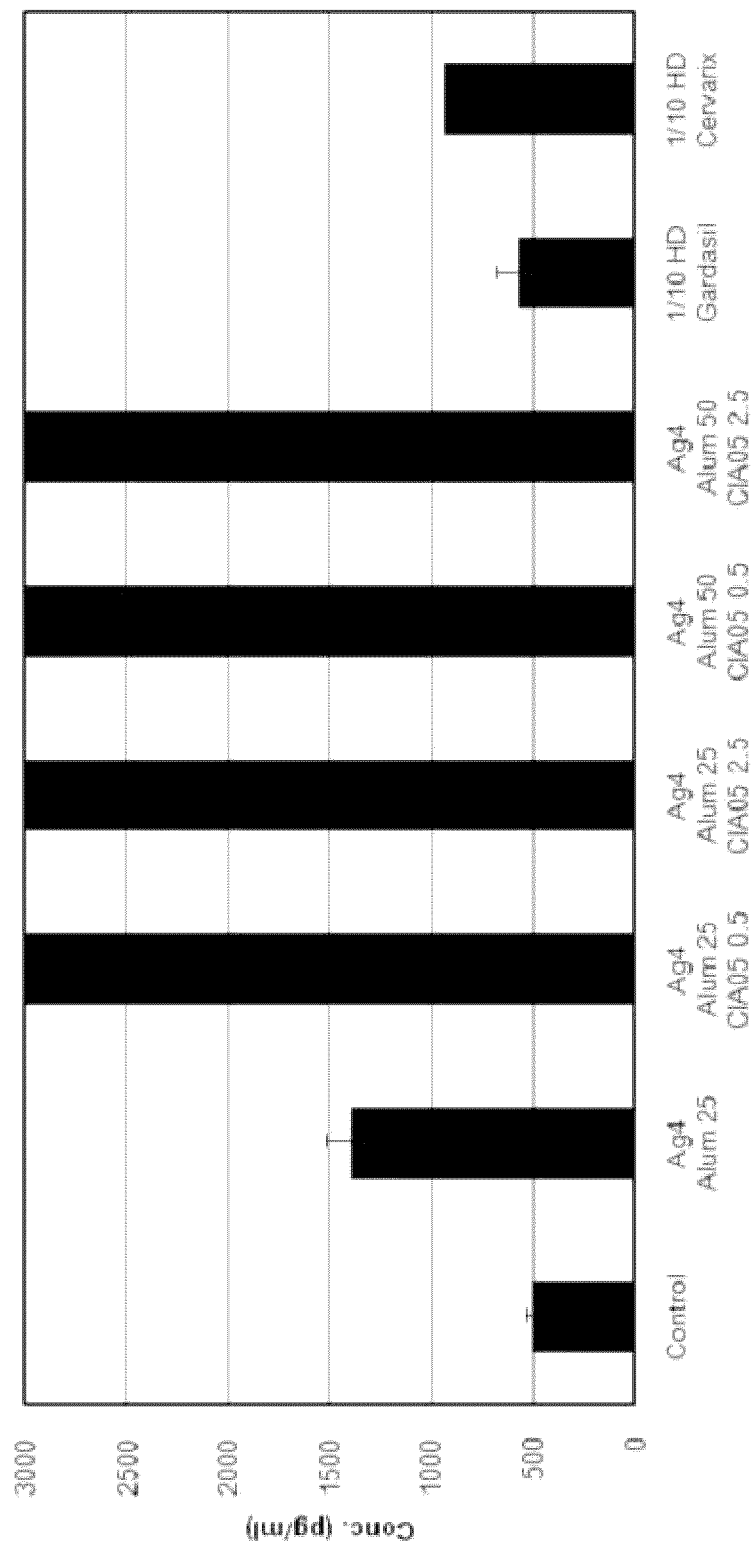
FIG. 30 is a graph showing the excretion level of of INF-γ from spleen cells depending on the various concentrations of novel CIA05, HPV 16/18 L1 VLP and aluminum peroxide (Alum) in the combination mixture.

In addition, as shown in FIG. 30, the level of INF-γ excreted from mouse spleen cells was higher when the adjuvant CIA05 and Alum were administered together than Alum administered alone. The INF-γ expression level was greater than Cervarix™ and Gardasil™ treated groups.

In FIG. 26-29, the vaccine comprises of HPV16 L1 VLP and HPV18 L1 VLP, aluminum hydroxide and CAI05, whereas CIA05 is substituted to MPL in Cervarix manufactured by GSK. Thus, it is clear that CIA05 from this invention has lesser toxicity and higher immune stimulating effect when compare to MPL.

In summary, result shows that the experimental group treated with HPV16 L1 VLP and HPV18 L1 VLP, combined with the adjuvant CIA05 developed by the inventors had greater immunization effect compare to the group immunized with conventional cervical cancer vaccine. Considering the dispute on the prolonged effect of conventional cervical cancer vaccines, increasing the immune stimulating effect by combining an adjuvant is a creative and advanced method for solving this problem.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for preventing human cervical cancer, comprising administering to a human a pharmaceutical composition comprising (a) (i) an L1 virus-like particle (VLP) of human papillomavirus (HPV) type 16, an L1 VLP of HPV type 18, or a combination thereof; and (ii) CIA05 as a deacylated non-toxic lipooligosaccharide (LOS), which is detoxificated by deacylation of lipid A of lipopolysaccharide isolated from *E. coli* (*Escherichia coli*); (b) a pharmaceutically acceptable carrier; and (c) aluminum hydroxide, with the proviso that the composition does not include bacterial DNA as an adjuvant.

2. The method according to claim 1, wherein the L1 VLP of HPV type 16 or 18 is obtained through a purification procedure, comprising the steps of: (i) culturing yeasts containing a nucleotide sequence encoding the L1 of HPV type 16 or 18; (ii) lysing the cultured yeast; (iii) eliminating impurities by precipitating the yeast lysate with ammonium sulfate; and (iv) performing a heparin chromatography or cation-exchange chromatography in the yeast lysate which the impurities are removed.

3. The method according to claim 1, wherein the non-toxic LOS is detoxificated by deacylation of lipid A via alkaline treatment to LPS (lipopolysaccharide).

4. The method according to claim 1, wherein the pharmaceutical composition further comprises an immunoadjuvant which is: a Group II element selected from the group consisting of Mg, Ca, Sr, Ba and Ra; a Group IV element selected from the group consisting of Ti, Zr, Hf and Rf; or an aluminium salt or a hydrate thereof.

5. The method according to claim 1, wherein the pharmaceutical composition comprises an L1 VLP of HPV type 16 and an L1 VLP of HPV type 18.

* * * * *